United States Patent
Luly et al.

(12) 
(10) Patent No.: US 6,613,905 B1
(45) Date of Patent: Sep. 2, 2003

(54) CHEMOKINE RECEPTOR ANTAGONISTS AND METHODS OF USE THEREFOR

(75) Inventors: Jay R. Luly, Wellesley, MA (US); Yoshisuke Nakasato, Shizuoka (JP); Etsuo Ohshima, Shizuoka (JP)

(73) Assignees: Millennium Pharmaceuticals, Inc., Cambridge, MA (US); Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/148,823

(22) Filed: Sep. 4, 1998

Related U.S. Application Data

(63) Continuation-in-part of application No. 09/010,320, filed on Jan. 21, 1998, now abandoned.

(51) Int. Cl.[7] .................... C07D 405/06; C07D 223/18; A61P 37/00
(52) U.S. Cl. .................. 546/196; 546/197; 546/202; 546/203; 540/522; 514/320; 514/319; 514/321; 514/324; 514/217
(58) Field of Search ................. 546/196, 197, 546/202, 203; 514/320, 319, 321, 324, 217; 540/522

(56) References Cited

U.S. PATENT DOCUMENTS

| | | | |
|---|---|---|---|
| 3,409,621 A | 11/1968 | Villani et al. | 260/268 |
| 3,770,729 A | 11/1973 | Nakanishi et al. | 260/240 |
| 4,042,695 A * | 8/1977 | Buus et al. | 424/250 |
| 4,250,176 A | 2/1981 | Vandenberk et al. | 424/250 |
| 4,335,122 A | 6/1982 | McFadden et al. | 424/244 |
| 4,547,496 A | 10/1985 | Kumazawa et al. | 514/218 |
| 4,567,178 A | 1/1986 | Eberlein et al. | 514/215 |
| 4,645,758 A | 2/1987 | Willman et al. | 514/239 |
| 4,994,463 A | 2/1991 | Oshima et al. | 514/253 |
| 4,999,363 A | 3/1991 | Oshima et al. | 514/332 |
| 5,010,087 A | 4/1991 | Oshima et al. | 514/307 |
| 5,010,104 A | 4/1991 | Oshima et al. | 514/510 |
| 5,011,836 A | 4/1991 | Eberlein et al. | 514/217 |
| 5,089,496 A | 2/1992 | Piwinski et al. | 514/253 |
| 5,116,863 A * | 5/1992 | Oshima | 514/450 |
| 5,118,701 A | 6/1992 | Oshima et al. | 514/395 |
| 5,143,922 A * | 9/1992 | Oshima et al. | 514/320 |
| 5,239,083 A | 8/1993 | Kumazawa et al. | 548/465 |
| 5,242,931 A | 9/1993 | Oshima et al. | 514/307 |
| 5,302,596 A | 4/1994 | Ohshima et al. | 514/261 |
| 5,302,602 A | 4/1994 | Oshima et al. | 514/325 |
| 5,340,807 A | 8/1994 | Kumazawa et al. | 514/215 |
| 5,378,701 A | 1/1995 | Ohshima et al. | 514/215 |
| 5,478,835 A | 12/1995 | Kumazawa et al. | 514/290 |
| 5,478,840 A | 12/1995 | Ohshima et al. | 514/303 |
| 5,538,986 A | 7/1996 | Ting et al. | 514/337 |
| 5,607,955 A | 3/1997 | Ohshima et al. | 514/359 |
| 5,672,611 A | 9/1997 | Doll et al. | 514/325 |
| 5,679,703 A | 10/1997 | Yanase et al. | 514/431 |
| 5,688,788 A | 11/1997 | Andersen et al. | 514/211 |
| 5,801,175 A | 9/1998 | Afonso et al. | 514/254 |
| 5,874,428 A * | 2/1999 | Dorwald | 514/217 |
| 5,877,177 A | 3/1999 | Taveras | 514/254 |
| 5,919,776 A * | 7/1999 | Hagmann | 514/159 |
| 6,040,318 A | 3/2000 | Andersen et al. | 514/329 |
| 6,048,856 A | 4/2000 | Jørgensen et al. | 514/217 |
| 6,150,355 A | 11/2000 | Kumazawa et al. | 514/215 |

FOREIGN PATENT DOCUMENTS

| | | |
|---|---|---|
| CH | 421 138 A | 3/1967 |
| CS | 240 698 | 6/1987 |
| DE | 80449 | 9/1969 |
| DE | 1 918 739 | 10/1969 |
| DE | 3326641 A1 | 2/1984 |
| EP | 0309422 A2 | 3/1989 |
| EP | 0341860 A1 | 11/1989 |
| EP | 0515158 A1 | 11/1992 |
| EP | 0524784 A1 | 1/1993 |
| EP | 0916668 A1 | 5/1999 |
| GB | 1 003 292 | 9/1965 |
| GB | 1109847 | 4/1968 |
| GB | 1213172 | 11/1970 |
| GB | 1 330 966 | 9/1973 |
| JP | 61167663 | 7/1986 |
| JP | 9040662 | 2/1997 |
| WO | WO 89/10369 | 11/1989 |
| WO | WO 92/16226 | 10/1992 |
| WO | WO 92/20681 | 11/1992 |
| WO | WO 93/02081 | 2/1993 |
| WO | WO 96/31469 | 10/1996 |
| WO | WO 96/31470 | 10/1996 |
| WO | WO 96/31477 | 10/1996 |
| WO | WO 96/31498 | 10/1996 |
| WO | WO 97/24325 | 7/1997 |
| WO | WO 97/44329 | 11/1997 |
| WO | WO 98/02151 | 1/1998 |
| WO | WO 98/04554 | 2/1998 |
| WO | WO 98/11092 | 3/1998 |
| WO | WO 98/11093 | 3/1998 |
| WO | WO 98/11096 | 3/1998 |
| WO | WO 98/11097 | 3/1998 |

(List continued on next page.)

OTHER PUBLICATIONS

Ting, P.C. et al., Chemical Abstracts, 123: 227838 (1995).
Kumazawa, T. et al., Chemical Abstracts, 126: 212158 (1997).

(List continued on next page.)

*Primary Examiner*—Evelyn Mei Huang
(74) *Attorney, Agent, or Firm*—Hamilton, Brook, Smith & Reynolds, P.C.

(57) ABSTRACT

Disclosed are novel compounds and a method of treating a disease associated with aberrant leukocyte recruitment and/or activation. The method comprises administering to a subject in need an effective amount of a compound represented by the following structural formula:

$$Z{=}{\overset{}{\underset{}{}}}(CH_2)_n{-}N\phantom{xx}M;$$

and physiologically acceptable salts thereof.

9 Claims, 19 Drawing Sheets

FOREIGN PATENT DOCUMENTS

| WO | WO 98/11098 | 3/1998 |
|----|-------------|--------|
| WO | WO 98/11099 | 3/1998 |
| WO | WO 98/11106 | 3/1998 |
| WO | WO 98/15546 | 4/1998 |
| WO | WO 98/25604 | 6/1998 |
| WO | WO 98/25605 | 6/1998 |
| WO | WO 98/25617 | 6/1998 |
| WO | WO 98/27815 | 7/1998 |
| WO | WO 98/43638 | 10/1998 |
| WO | WO 98/46587 | 10/1998 |
| WO | WO 99/37617 | 7/1999 |
| WO | WO 99/37619 | 7/1999 |
| WO | WO 99/37651 | 7/1999 |
| WO | WO 00/14089 | 3/2000 |

OTHER PUBLICATIONS

Kato, K. et al., Chemical Abstracts, 130: 237480 (1999).
Davis, M.A. et al., Chemcial Abstracts, 67: 99959 (1967).
Kukla, Michael J., Chemical Abstracts, 92: 198282 (1980).
Protiva, M. et al., Chemical Abstracts, 72: 3387 (1970).
Protiva, M. et al., Chemical Abstracts, 109: 92794 (1988).
Protiva, M. et al., Chemical Abstracts, 104: 19527 (1986).
Protiva, M. et al., Chemical Abstracts, 107: 134327 (1987).
Sindelar, K. et al., Chemical Abstracts, 104: 33990 (1986).
Michaels, R.J. et al., Chemical Abstracts, 77: 88537 (1972).
King, Frank D., "Bioisosteres, Conformational Restriction, and Pro–drugs–Case History: An Example of a Conformational Restriction Approach," *Medicinal Chemistry: Principles and Practice*, Chapter 14, p. 206–208.
Davis, M. A. et al., "New Psychotropic Agents.VIII Analogs of Amitriptyline Containing Normeperidine Group," *New Psychotropic Agents VIII.*, pp. 627–635 (1967, Jul.).
Helwig, H., et al., " Helwig/Otto Arzneimittal", *Arzneimittal*, 1:4–1 through 4–24, 8th Ed., (1992).
Sindelar, Karel, et al., "Potential Antidiarrheal Agents: 1–(11–Cyano–6,11–Dihydrodibenzo[b,e]Thiepin–11YL–Alklyl)—And 1–(10–Cyano–10,11–Dihydrodibenzo[b,f]Thiepin–10–yl–Alkyl) –4–Substituted Piperidines," *Collection Czechoslovak Chem. Commun.*, 50:1089–1096 (1985).
Chemical Abstracts, 121(3) :35275n (1994).
Sindelar, Karel, et al., "Antihistamine Substances: Tricyclic Analogues of N–(4,4–Diphenyl–3Butene–1yl)Nipecotic Acid and Some Related Compounds," *Collection Czechoslovak Chem. Commun.*,59:667–674 (1994).
Ali, Fadia E., et al., "Orally Active and Potent Inhibitors of γ–Aminobutyric Acid Uptake," *J. Med. Chem.* 28:653–660 (1985).
Sindelar, Karel, et al., "Potential Antihistaminics: Tricyclic Carboxylic Acids Derived from 6,11–Dihydrodibenzo[b,e] Thiepine and 4,9–Dihydrothieno[2,3–c]–2–Benzothiepine," *Collection Czechoslovak Chem. Commun.* 56:2482–2493 (1991).
Polivka, Zdenek, et al., "Heterocyclic Ethers Derived From 6,11–Dihydrodibenzo–[b,e]Thiepin–11–Ols and 4,9–Dihydrothieno[2,3–c]–2–Benzothiepin–4–Ol; A New Series of Potential Antidepressants and Antihistamine Agents," *Collection Czechoslovak Chem. Commun.* 51:2034–2049 (1986).
Polivka, Zdenek, et al., "Antiaminic Agents Derived From Thieno[2,3–c]–2–Benzothiepin: 4–(1–Methyl–4–Piperidylidene)–4,9–Dihydrothieno[2,3–c] –2–Benzothiepin and Some Related Compounds," *Collection Czechoslovak Chem. Commun.* 48:623–641 (1983).
Rajsner, M., et al., "Neurotropic and Psychotropic Comounds.XXXI Chemistry and Pharmacology of 11–(3–Dimethylaminopropylidene)–2–Mehtyl–6,11–Dihydrodibenzo[b,e] Thiepin and of Some Analogues," *Collection Czechoslovak Chem. Commun.* 34:1015–1024 (1969).
Rajsner, M., et al., "Neurotrope Und Psychotrope Substanzen XV. 4,9–Dihydrothieno[2,3–b]Benzo[e]Thiepin–Derivate," *Collection Czechoslovak Chem. Commun.* 32:2854–2866 (1967).
Hesselgesser, Joseph, et al., "Identification and Characterization of Small Molecule Functional Antagonists of the CCR1 Chemokine Receptor", *The Journal of Biological Chemistry*, 273(25) :15687–15692 (Jun. 19, 1998).
Chemical Abstracts, 93(19), 186323f (1980).
Chemical Abstracts, 77(25), 164662h (1972).
Chemical Abstracts, 82(5)k, 25566Z (1974).
Foldeak S et al. Tetrahedron. 41(24), 5913–18, 1985.*
Iorio LC et al. J. Pharmacol. Exp. Ther. 258(1), 118–23, 1991.*
Aftab DT et al. Mol. Pharmacol. 40(5), 798–805, 1991.*
Howard OMZ et al. TIBTECH. (1996) 14, 46–51.*
S.J. Rappaport, Ed., "Inflammation and Phagocytosis," In: *Pysiological Basis of Medical Practice, Twelfth Edition*, J.B. West, Eds., Williams & Wilkins, Baltimore, pp. 362–368 (1990).
Schmelz, M. and Petersen, L.J., "Neurogenic Inflammation in Human and Rodent Skin," *News Physiol. Sci.*, 16:33–37 (2001).

* cited by examiner

Example 1

Example 2

Example 4

Example 5

Example 6

Example 7

Example 8

Example 9

Example 10

Example 11

Example 12

Example 21　　Example 22　　Example 23

Example 24　　Example 25

Example 26　　Example 27

Example 28　　Example 29

Example 30　　Example 31

Example 32

Example 33

Example 34

Example 35

Example 36

Example 37

Example 38

Example 39

Example 40

Example 41

Example 42

Example 43

Example 44

Example 45

Example 46

Example 47

Example 48

Example 49

Example 50

Example 51

Example 52

Example 53

Example 54

Example 55

Example 56

Example 57

Example 58

Example 59

Example 60

Example 61

Example 62

Example 63

Example 64

Example 65

Example 66

Example 67

Example 68

Example 69

Example 70

Example 71

Example 72

Example 73

Example 74

Example 103

Example 104

Example 105

Example 106

Example 107

Example 108

Example 109

Example 110

Example 111

Example 112

CHEMOKINE RECEPTOR ANTAGONISTS AND METHODS OF USE THEREFOR

RELATED APPLICATIONS

This application is a continuation-in-part of U.S. Ser. No. 09/010,320, filed Jan. 21, 1998, now abandoned the entire teachings of which are hereby incorporated by reference.

BACKGROUND OF THE INVENTION

Chemoattractant cytokines or chemokines are a family of proinflammatory mediators that promote recruitment and activation of multiple lineages of leukocytes and lymphocytes. They can be released by many kinds of tissue cells after activation. Continuous release of chemokines at sites of inflammation mediates the ongoing migration of effector cells in chronic inflammation. The chemokines characterized to date are related in primary structure. They share four conserved cysteines, which form disulfide bonds. Based upon this conserved cysteine motif, the family is divided into two main branches, designated as the C—X—C chemokines (α-chemokines), and the C—C chemokines (β-chemokines), in which the first two conserved cysteines are separated by an intervening residue, or adjacent respectively (Baggiolini, M. and Dahinden, C. A., *Immunology Today*, 15:127–133 (1994)).

The C—X—C chemokines include a number of potent chemoattractants and activators of neutrophils, such as interleukin 8 (IL-8), PF4 and neutrophil-activating peptide-2 (NAP-2). The C—C chemokines include RANTES (Regulated on Activation, Normal T Expressed and Secreted), the macrophage inflammatory proteins 1α and 1β (MIP-1α and MIP-1β), eotaxin and human monocyte chemotactic proteins 1–3 (MCP-1, MCP-2, MCP-3), which have been characterized as chemoattractants and activators of monocytes or lymphocytes but do not appear to be chemoattractants for neutrophils. Chemokines, such as RANTES and MIP-1α, have been implicated in a wide range of human acute and chronic inflammatory diseases including respiratory diseases, such as asthma and allergic disorders.

The chemokine receptors are members of a superfamily of G protein-coupled receptors (GPCR) which share structural features that reflect a common mechanism of action of signal transduction (Gerard, C. and Gerard, N. P., *Annu Rev. Immunol.*, 12:775–808 (1994); Gerard, C. and Gerard, N. P., *Curr. Opin. Immunol.*, 6:140–145 (1994)). Conserved features include seven hydrophobic domains spanning the plasma membrane, which are connected by hydrophilic extracellular and intracellular loops. The majority of the primary sequence homology occurs in the hydrophobic transmembrane regions with the hydrophilic regions being more diverse. The first receptor for the C—C chemokines that was cloned and expressed binds the chemokines MIP-1α and RANTES. Accordingly, this MIP-1α/RANTES receptor was designated C—C chemokine receptor 1 (also referred to as CCR-1; Neote, K., et al., *Cell*, 72:415–425 (1993); Horuk, R. et al., WO 94/11504, May 26, 1994; Gao, J.-I. et al., *J. Exp. Med.*, 177:1421–1427 (1993)). Three receptors have been characterized which bind and/or signal in response to RANTES: CCR3 mediates binding and signaling of chemokines including eotaxin, RANTES, and MCP-3 (Ponath et al., *J. Exp. Med.*, 183:2437 (1996)), CCR4 binds chemokines including RANTES, MIP-1α, and MCP-1 (Power, et al., *J. Biol. Chem.*, 270:19495 (1995)), and CCR5 binds chemokines including MIP-1α, RANTES, and MIP-1β (Samson, et al., *Biochem.* 35: 3362–3367 (1996)). RANTES is a chemotactic chemokine for a variety of cell types, including monocytes, eosinophils, and a subset of T-cells. The responses of these different cells may not all be mediated by the same receptor, and it is possible that the receptors CCR1, CCR4 and CCR5 will show some selectivity in receptor distribution and function between leukocyte types, as has already been shown for CCR3 (Ponath et al.). In particular, the ability of RANTES to induce the directed migration of monocytes and a memory population of circulating T-cells (Schall, T. et al., *Nature*, 347:669–71 (1990)) suggests this chemokine and its receptor(s) may play a critical role in chronic inflammatory diseases, since these diseases are characterized by destructive infiltrates of T cells and monocytes.

Many existing drugs have been developed as antagonists of the receptors for biogenic amines, for example, as antagonists of the dopamine and histamine receptors. No successful antagonists have yet been developed to the receptors for the larger proteins such as chemokines and C5a. Small molecule antagonists of the interaction between C—C chemokine receptors and their ligands, including RANTES and MIP-1α, would provide compounds useful for inhibiting harmful inflammatory processes "triggered" by receptor ligand interaction, as well as valuable tools for the investigation of receptor-ligand interactions.

SUMMARY OF THE INVENTION

It has now been found that a class of small organic molecules are antagonists of chemokine receptor function and can inhibit leukocyte activation and/or recruitment. An antagonist of chemokine receptor function is a molecule which can inhibit the binding and/or activation of one or more chemokines, including C—C chemokines such as RANTES, MIP-1α, MCP-2, MCP-3 and MCP-4 to one or more chemokine receptors on leukocytes and/or other cell types. As a consequence, processes and cellular responses mediated by chemokine receptors can be inhibited with these small organic molecules. Based on this discovery, a method of treating a disease associated with aberrant leukocyte recruitment and/or activation is disclosed as well as a method of treating a disease mediated by chemokine receptor function. The method comprises administering to a subject in need an effective amount of a compound or small organic molecule which is an antagonist of chemokine receptor function. Compounds or small organic molecules which have been identified as antagonists of chemokine receptor function are discussed in detail hereinbelow, and can be used for the manufacture of a medicament for treating or for preventing a disease associated with aberrant leukocyte recruitment and/or activation. The invention also relates to the disclosed compounds and small organic molecules for use in treating or preventing a disease associated with aberrant leukocyte recruitment and/or activation. The invention also includes pharmaceutical compositions comprising one or more of the compounds or small organic molecules which have been identified herein as antagonists of chemokine function and a suitable pharmaceutical carrier. The invention further relates to novel compounds which can be used to treat an individual with a disease associated with aberrant leukocyte recruitment and/or activation and methods for their preparation.

DETAILED DESCRIPTION OF THE INVENTION

Figure 1:
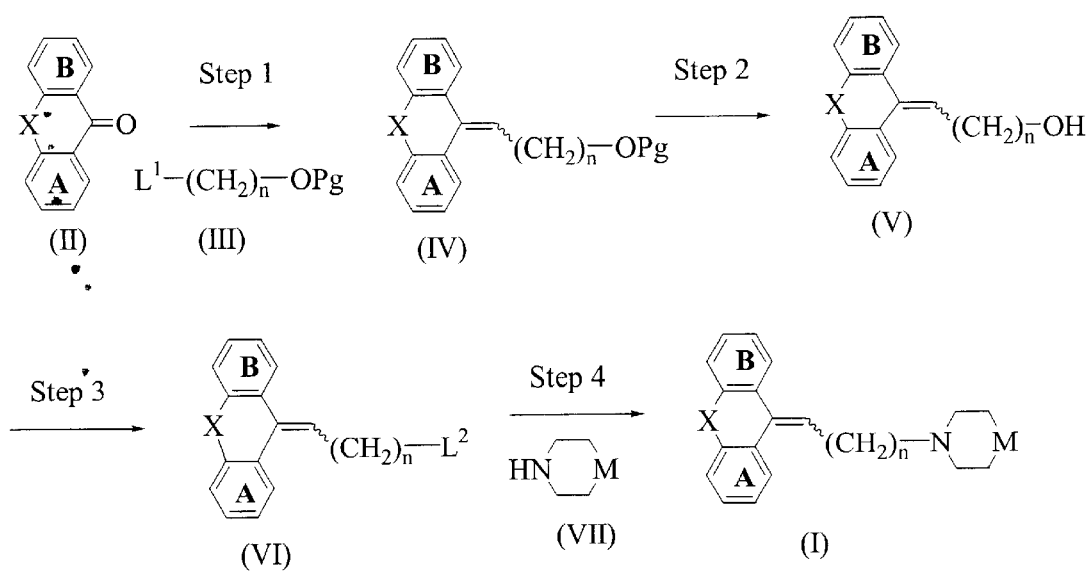
FIG. 1 is a schematic showing the preparation of the compounds represented by Structural Formula (I).

The present invention relates to small molecule compounds which are modulators of chemokine receptor function. In a preferred embodiment, the small molecule compounds are antagonists of chemokine receptor function. Accordingly, processes or cellular responses mediated by the binding of a chemokine to a receptor can be inhibited (reduced or prevented, in whole or in part), including leukocyte migration, integrin activation, transient increases in the concentration of intracellular free calcium $[Ca^{++}]_i$, and/or granule release of proinflammatory mediators.

The invention further relates to a method of treatment, including prophylactic and therapeutic treatments, of a disease associated with aberrant leukocyte recruitment and/or activation or mediated by chemokines or chemokine receptor function, including chronic inflammatory disorders characterized by the presence of RANTES, MIP-1α, MCP-2, MCP-3 and/or MCP-4 responsive T cells, monocytes and/or eosinophils, including but not limited to diseases such as arthritis, psoriasis, multiple sclerosis, inflammatory bowel diseases such as ulcerative colitis and Crohn's disease, rejection of transplanted organs and tissues (i.e., allograft rejection), graft versus host disease, as well as allergies and asthma. Other diseases associated with aberrant leukocyte recruitment and/or activation which can be treated (including prophylactic treatments) with the methods disclosed herein are inflammatory diseases associated with Human Immunodeficiency Virus (HIV) infection, e.g., AIDS associated encephalitis, AIDS related maculopapular skin eruption, AIDS related interstitial pneumonia, AIDS related enteropathy, AIDS related periportal hepatic inflammation and AIDS related glomerulo nephritis. The method comprises administering to the subject in need of treatment an effective amount of a compound (i.e., one or more compounds) which inhibits chemokine receptor function, inhibits the binding of a chemokine to leukocytes and/or other cell types, and/or which inhibits leukocyte migration to, and/or activation at, sites of inflammation.

The invention further relates to methods of antagonizing a chemokine receptor, such as CCR1, in a mammal comprising administering to the mammal a compound as described herein.

According to the method, chemokine-mediated chemotaxis and/or activation of pro-inflammatory cells bearing receptors for chemokines can be inhibited. As used herein, "pro-inflammatory cells" includes but is not limited to leukocytes, since chemokine receptors can be expressed on other cell types, such as neurons and epithelial cells.

While not wishing to be bound by any particular theory or mechanism, it is believed that compounds of the invention are antagonists of the chemokine receptor CCR1, and that therapeutic benefits derived from the method of the invention are the result of antagonism of CCR1 function. Thus, the method and compounds of the invention can be used to treat a medical condition involving cells which express CCR1 on their surface and which respond to signals transduced through CCR1, as well as the specific conditions recited above.

The antagonist of chemokine receptor function is represented by Structural Formula (I):

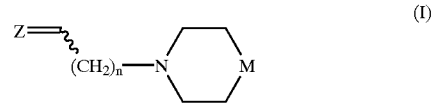

(I)

and physiologically acceptable salts thereof.

Z is a cycloalkyl or non-aromatic heterocyclic ring group fused to one, two or more aromatic rings, wherein each ring in Z is independently substituted or unsubstituted.

n is an integer, such as an integer from one to about four. Preferably, n is one, two or three. More preferably n is two. In alternative embodiments, other aliphatic or aromatic spacer groups (L) can be employed for $(CH_2)_n$.

M is $>NR^2$ or $>CR^1R^2$. M is preferably $>C(OH)R^2$.

$R^1$ is —H, —OH, an aliphatic group, —O-(aliphatic group), —O-(substituted aliphatic group), —SH, —S-(aliphatic group), —S-(substituted aliphatic group), —OC(O)-(aliphatic group) or —O—C(O)-(substituted aliphatic group), —COOH, —CN, —CO—$NR^3R^4$ or —$NR^3R^4$. $R^1$ is preferably —H or —OH.

$R^2$ is —H, —OH, an acyl group, a substituted acyl group, —$NR^5R^6$, an aliphatic group, a substituted aliphatic group, an aromatic group, a substituted aromatic group, a benzyl group, a substituted benzyl group, a non-aromatic heterocyclic group or a substituted non-aromatic heterocyclic group. $R^2$ is preferably an aromatic group or a substituted aromatic group.

$R^3$, $R^4$, $R^5$ and $R^6$ are independently —H, an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group.

$R^1$ and $R^2$, $R^3$ and $R^4$, or $R^5$ and $R^6$ taken together with the atom to which they are bonded, can alternatively form a substituted or unsubstituted non-aromatic carbocyclic or heterocyclic ring.

In one preferred embodiment, Z is a tricyclic ring system comprising two carbocyclic aromatic groups fused to a six, seven or eight membered cycloalkyl group or to a non-aromatic heterocyclic ring. In one example, Z is represented by Structural Formula (II):

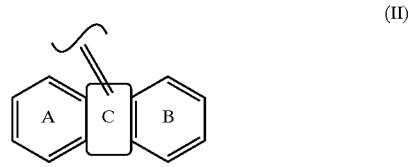

(II)

The phenyl rings in Structural Formula (II), labeled with an "A" and "B", are referred to herein as "Ring A" and "Ring B", respectively. The central ring, labeled with a "C", is referred to as "Ring C" and can be, for example, a seven or eight membered non-aromatic carbocyclic ring (e.g., a cycloheptane or cyclooctane ring) or a non-aromatic heterocyclic ring. When Ring C is a non-aromatic heterocyclic ring, it can contain one or two heteroatoms such as nitrogen, sulfur or oxygen. When Z is represented by Structural Formula (II), the tricyclic ring system can be connected to the remainder of the molecule by a covalent double bond between a carbon atom in Ring C and the carbon atom which, as depicted in Structural Formula (I), is bonded to Z.

Ring A and/or Ring B in Structural Formula (II) can be unsubstituted. Alternatively, Ring A and/or Ring B can have one or more substituents. Suitable substituents are as described hereinbelow. In one example, Ring A or Ring B is substituted with —$(O)_u$—$(CH_2)_t$—$COOR^{20}$, —$(O)_u$—$(CH_2)_t$—$C(O)$—$NR^{21}R^{22}$ or —$(O)_u(CH_2)_t$—$NHC(O)O$—$R^{20}$.

u is zero or one.

t is an integer, such as an integer from zero to about three, and the methylene group —$(CH_2)_t$— can be substituted or unsubstituted.

$R^{20}$, $R^{21}$ or $R^{22}$ are independently —H, an aliphatic group, a substituted aliphatic group, an aromatic group, a substituted aromatic group or a non-aromatic heterocyclic group. Alternatively, $R^{21}$ and $R^{22}$, taken together with the nitrogen atom to which they are bonded, can form a non-aromatic heterocyclic ring.

Ring C optionally contains one or more substituents, as described hereinbelow.

Examples of suitable tricyclic ring systems, Z, are provided by Structural Formula (III):

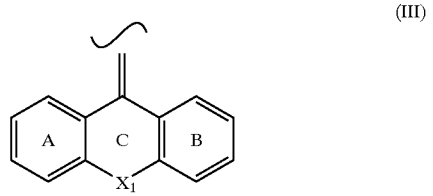

(III)

Ring A and Ring B in Structural Formula (III) are as described for Structural Formula (II).

$X_1$ is —S—, —$CH_2$—, —$CH_2$—$CH_2$—, —$CH_2$—S—, —S—$CH_2$—, —O—$CH_2$—, —$CH_2$—O—, —$NR_c$—$CH_2$—, —$CH_2$—$NR_c$—, —SO—$CH_2$—, —$CH_2$—SO—, —$S(O)_2$—, $CH_2$—, —$CH_2$—$S(O)_2$—, —CH=CH—, —$NR_c$—CO— or —CO—$NR_c$—. Preferably $X_1$ is —$CH_2$—O—, —$CH_2$—$CH_2$—, —$CH_2$—S—, —$NR_c$—CO— or —CO—$NR_c$—.

$R_c$ is hydrogen, an aliphatic group, a substituted aliphatic group, an aromatic group, a substituted aromatic group, a benzyl group or a substituted benzyl group.

In one example, $R_c$ is —$(CH_2)_s$—$COOR^{30}$, —$(CH_2)_s$—$C(O)$—$NR^{31}R^{32}$ or —$(CH_2)_s$—$NHC(O)$—O—$R^{30}$, wherein s is an integer, such as an integer from one to about three; $R^{30}$, $R^{31}$ and $R^{32}$ are independently —H, an aliphatic group, a substituted aliphatic group, an aromatic group, a substituted aromatic group or a non-aromatic heterocyclic group. Alternatively, $R^{31}$ and $R^{32}$, taken together with the nitrogen atom to which they are bonded, form a non-aromatic heterocyclic ring.

Other examples of suitable tricyclic ring systems for Z include benzodiazepines, benzooxazepines, benzooxazines, phenothiazines and groups represented by the following structural formulas:

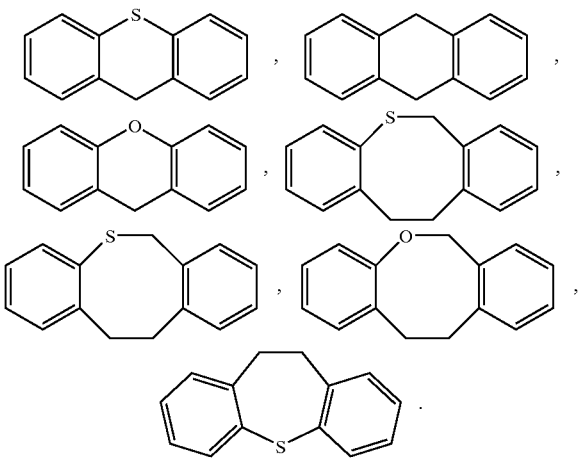

In another preferred embodiment, Z is a tricyclic ring system comprising two aromatic groups fused to a seven or eight membered cycloalkyl group or to a non-aromatic heterocyclic ring, wherein at least one of the aromatic groups is a heteroaryl group. In one example, Z is represented by Structural Formula (IV):

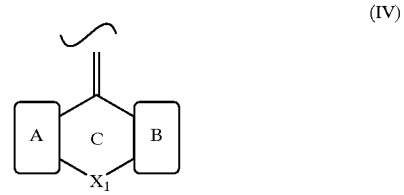

(IV)

Ring A in Structural Formula (IV) can be a substituted or unsubstituted heteroaryl group. Ring B in Structural Formula (IV) can be a substituted or unsubstituted aromatic group, e.g., a heteroaryl group or carbocyclic aryl group. Suitable substituents are as described hereinbelow. In one example, Ring A and/or Ring B is substituted with —$(O)_u$—$(CH_2)_t$—$COOR^{20}$, —$(O)_u$—$(CH_2)_t$—$C(O)$—$NR^{21}R^{22}$ or —$(O)_u(CH_2)_t$—$NHC(O)O$—$R^{20}$ as described above. u, t, $R^{20}$, $R^{21}$, and $R^{22}$ are as described above. $X_1$ and $R_c$ can be as described above for Structural Formula (III).

In another embodiment of the present invention Z is represented by Structural Formula (IV), wherein Ring A is a pyridyl group and Ring B is an aromatic or heteroaromatic group. In this embodiment Ring A and Ring B are independently substituted or unsubstituted, and Ring B is preferably a phenyl group. $X_1$ and $R_c$ can be as described above for Structural Formula (III).

In another embodiment of the present invention Z is represented by Structural Formula (V):

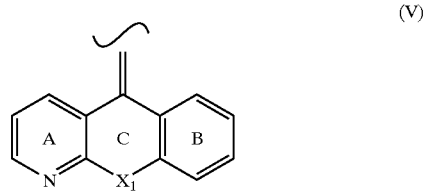

(V)

Ring A and Ring B can be independently substituted or unsubstituted as described above in Structural Formula (II), and $X_1$ can be as described above for Structural Formula (III).

In a preferred embodiment Ring B in Structural Formula (V) is substituted para to the carbon atom of Ring B which is bonded to $X_1$ of Ring C, and Z is represented by Structural Formula (VI):

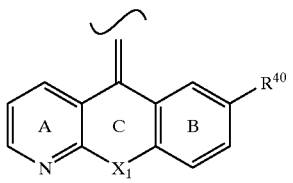

(VI)

$X_1$ can be as described above in Structural Formula (II). Preferably $X_1$ is —$CH_2$—O—, —$CH_2$—$CH_2$— or —$CH_2$—S—.

$R^{40}$ is a substituent as described hereinbelow. Preferably $R^{40}$ is an aliphatic group, —O-(aliphatic group) or —O-(substituted aliphatic group). More preferably $R^{40}$ is an —O-alkyl, such as —O—$CH_3$, —O—$C_2H_5$, —O—$C_3H_7$ or —O—$C_4H_9$.

Another embodiment of the present invention includes novel compounds employed in these methods.

The compounds disclosed herein can be obtained as E- and Z-configurational isomers. It is expressly pointed out that the invention includes compounds of the E-configuration and the Z-configuration around the double bond connecting Ring C of Z to the remainder of the molecule, and a method of treating a subject with compounds of the E-configuration, the Z-configuration, and mixtures thereof. Accordingly, in the structural formulas presented herein, the symbol:

is used to represent both the E-configuration and the Z-configuration. Preferably Ring A and the alkylene chain bonded to Ring C are in the cis configuration. For example, the compounds can have the configuration of:

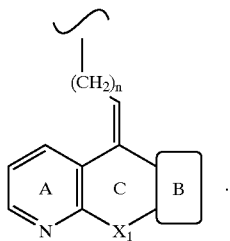

It is understood that one configuration can have greater activity than another. The desired configuration can be determined by screening for activity, employing the methods described herein.

Additionally, certain compounds of the invention may be obtained as different sterioisomers (e.g., diastereomers and enantiomers). It is pointed out that the invention includes all isomeric forms and racemic mixtures of the disclosed compounds and a method of treating a subject with both pure isomers and mixtures thereof, including racemic mixtures. Again, it is understood that one sterioisomer may be more active than another. The desired isomer can be determined by screening.

Also included in the present invention are physiologically acceptable salts of the compounds represented by Structural Formulas (I) through (IV). Salts of compounds containing an amine or other basic group can be obtained, for example, by reacting with a suitable organic or inorganic acid, such as hydrogen chloride, hydrogen bromide, acetic acid, citric acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium, ammonium, calcium and the like.

As used herein, aliphatic groups include straight chained, branched or cyclic $C_1$–$C_{20}$ hydrocarbons which are completely saturated or which contain one or more units of unsaturation. For example, suitable aliphatic groups include substituted or unsubstituted linear, branched or cyclic $C_1$–$C_{20}$ alkyl, alkenyl or alkynyl groups.

Aromatic groups include carbocyclic aromatic groups such as phenyl, 1-naphthyl, 2-naphthyl, 1-anthracyl and 2-anthracyl, and heterocyclic aromatic or heteroaryl groups such as N-imidazolyl, 2-imidazolyl, 4-imidazolyl, 5-imidazolyl, 2-thienyl, 3-thienyl, 2-furanyl, 3-furanyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 4-pyridazinyl, 3-pyrazolyl, 4-pyrazolyl, 5-pyrazolyl, 2-pyrazinyl, 2-thiazolyl, 4-thiazolyl, 5-thiazolyl, 5-tetrazolyl, 2-oxazolyl, 4-oxazolyl and 5-oxazolyl. Where these rings are fused, for example, to Ring C, the stated point of attachment can be either of the two fused bonds.

Aromatic groups also include fused polycyclic aromatic ring systems in which a carbocyclic aromatic ring or heteroaryl ring is fused to one or more other rings. Examples include tetrahydronaphthyl, 2-benzothienyl, 3-benzothienyl, 2-benzofuranyl, 3-benzofuranyl, 2-indolyl, 3-indolyl, 2-quinolinyl, 3-quinolinyl, 2-benzothiazolyl, 2-benzooxazolyl, 2-benzimidazolyl, 2-quinolinyl, 3-quinolinyl, 1-isoquinolinyl, 3-quinolinyl, 1-isoindolyl, 3-isoindolyl, and acridinyl. Also included within the scope of the term "aromatic group", as it is used herein, is a group in which one or more carbocyclic aromatic rings and/or heteroaryl rings are fused to a cycloalkyl or non-aromatic heterocyclic ring, for example, benzocyclopentane, benzocyclohexane.

Non-aromatic heterocyclic rings are non-aromatic carbocyclic rings which include one or more heteroatoms such as nitrogen, oxygen or sulfur in the ring. The ring can be five, six, seven or eight-membered and/or fused to another ring, such as a cycloalkyl on aromatic ring. Examples include 3-1H-benzimidazol-2-one, 3-1-alkyl-benzimidazol-2-one, 3-1-methyl-benzimidazol-2-one, 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidyl, 1-3-alkyl-phthalimidyl, benzoxane, benzopyrolidine, benzopiperidine, benzoxolane, benzothiolane, benzothiane,

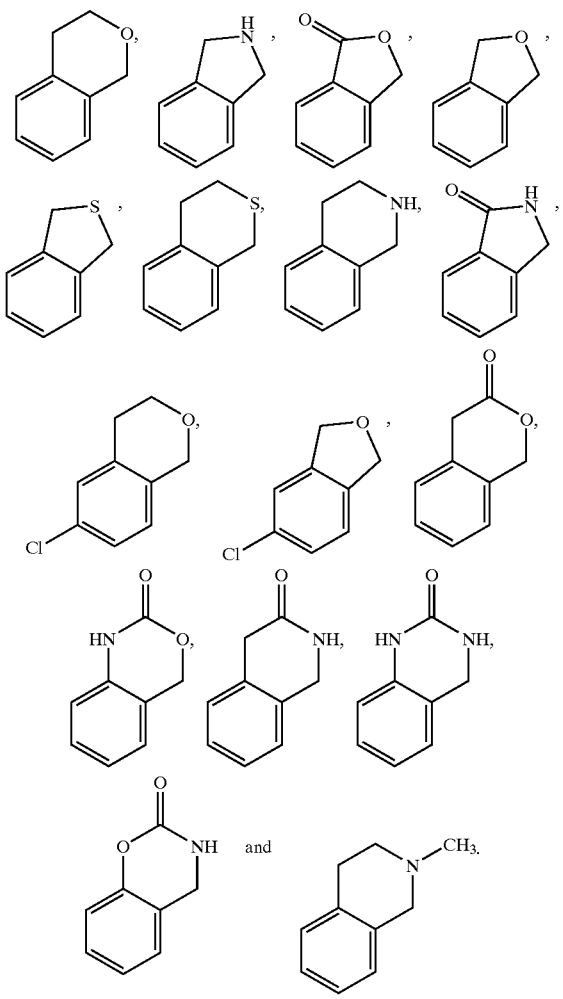

Suitable substituents on an aliphatic group, aromatic group (carbocyclic and heteroaryl), non-aromatic heterocyclic ring or benzyl group include, for example, an electron withdrawing group, a halogen, —CN, —COOH, —OH, —CNR$^{24}$R$^{25}$—, NR$^{24}$R$^{25}$, —OS(O)$_2$NR$^{24}$R$^{25}$, —S(O)$_{2-4}$NR$^{25}$, —SO$_3$H, —S(O)$_2$NH$_2$, guanidino, —(CH$_2$)$_t$—COOH, —(CH$_2$)$_t$—COOR$^{20}$, —(CH$_2$)$_t$—C(O)—NR$^{21}$R$^{22}$, —Q—H, —Q-(aliphatic group), —Q-(substituted aliphatic group), —Q-(aryl), —Q—(CH$_2$)$_p$-(substituted or unsubstituted aromatic group) (p is an integer from 1–5), —Q-(non-aromatic heterocyclic group) or —Q—(CH$_2$)$_p$-(non-aromatic heterocyclic group).

R$^{20}$, R$^{21}$ or R$^{22}$ are independently —H, an aliphatic group, a substituted aliphatic group, an aromatic group, a substituted aromatic group, —NHC(O)—O-(aliphatic group), —NHC(O)—O-(aromatic group) or —NHC(O)—O-(non-aromatic heterocyclic group) and wherein R$^{21}$ and R$^{22}$, taken together with the nitrogen atom to which they are bonded, can form a non-aromatic heterocyclic ring.

It is an integer from zero to about three.

Q is —O—, —S—, —S(O)—, —S(O)$_2$, —OS(O)$_2$—, —C(O)—, —OC(O)—, —C(O)O—, —C(O)C(O)—O—, —C—C(O)C(O)—, —C(O)NH—, —NHC(O)—, —OC(O)NH—, —NHC(O)O—, —NH—C(O)—NH—, —S(O)$_2$NH—, —NHS(O)$_2$—, —N(R$^{23}$)—, —C(NR$^{23}$)NHNH— or —NHNHC(NR$^{23}$)—.

R$^{23}$ is —H, an aliphatic group, a benzyl group, an aryl group or non-aromatic heterocyclic group.

R$^{24}$ and R$^{25}$ are independently —H, an aliphatic group, a benzyl group, an aryl group or non-aromatic heterocyclic group.

A substituted non-aromatic heterocyclic ring, benzyl group or aromatic group can also have an aliphatic or substituted aliphatic group, as a substituent. A substituted aliphatic group can also have an oxo group, epoxy group, non-aromatic heterocyclic ring, benzyl group, substituted benzyl group, aromatic group or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent.

Acyl groups include substituted and unsubstituted aliphatic carbonyl, aromatic carbonyl, aliphatic sulfonyl and aromatic sulfonyl.

Suitable electron withdrawing groups include, for example, alkylimines, alkylsulfonyl, carboxamido, carboxylic alkyl esters, —CH=NH, —CN, —NO$_2$ and halogens.

In the structural formulas depicted herein, the single or double bond by which a chemical group or moiety is connected to the remainder of the molecule or compound is indicated by the following symbol:

For example, the corresponding symbol in Structural Formulas (II), (III) and (IV) indicates the double bond by which the central ring of the tricyclic ring system is connected to the remainder of the molecule represented by Structural Formula (I).

A "subject" is preferably a bird or mammal, such as a human, but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

An "effective amount" of a compound is an amount which results in the inhibition of one or more processes mediated by the binding of a chemokine to a receptor in a subject with a disease associated with aberrant leukocyte recruitment and/or activation. Examples of such processes include leukocyte migration, integrin activation, transient increases in the concentration of intracellular free calcium [Ca$^{2+}$]$_i$ and granule release of proinflammatory mediators. Alternatively, an "effective amount" of a compound is a quantity sufficient to achieve a desired therapeutic and/or prophylactic effect, such as an amount which results in the prevention of or a decrease in the symptoms associated with a disease associated with aberrant leukocyte recruitment and/or activation.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compound can range from about 0.1 mg per day to about 100 mg per day for an adult. Preferably, the dosage ranges from about 1 mg per day to about 100 mg per day. An antagonist of chemokine receptor function can also be administered in combination with one or more additional therapeutic agents, e.g. theophylline, β-adrenergic bronchodilators, corticosteroids, antihistamines, antiallergic agents and the like.

The compound can be administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound can also be administered orally (e.g., dietary), transdermally, topically, by inhalation (e.g., intrabronchial, intranasal, oral inhalation or intranasal drops), or rectally, depending on the disease or condition to be treated. Oral or parenteral administration are preferred modes of administration.

The compound can be administered to the individual in conjunction with an acceptable pharmaceutical carrier as part of a pharmaceutical composition for treatment of HIV infection, inflammatory disease, or the other diseases discussed above. Formulation of a compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The activity of compounds of the present invention can be assessed using suitable assays, such as receptor binding assays and chemotaxis assays. For example, as described in the Exemplification Section, small molecule antagonists of RANTES and MIP-1α binding have been identified utilizing THP-1 cells which bind RANTES and chemotax in response to RANTES and MIP-1α as a model for leukocyte chemotaxis. Specifically, a high through-put receptor binding assay, which monitors $^{125}$I-RANTES and $^{125}$I-MIP-1α binding to THP-1 cell membranes, was used to identify small molecule antagonists which block binding of RANTES and MIP-1α. Compounds of the present invention can also be identified by virtue of their ability to inhibit the activation steps triggered by binding of a chemokine to its receptor, such as chemotaxis, integrin activation and granule mediator release. They can also be identified by virtue of their ability to block RANTES and MIP-1α mediated HL-60, T-cell, peripheral blood mononuclear cell, and eosinophil chemotactic response.

The compounds disclosed herein can be prepared accordingly to the schemes shown in FIGS. 1–5. The schemes are described in greater detail below.

FIG. 1 shows the preparation of compounds represented by Structural Formula (I). $L^1$ is PPh$_3$Cl, PPh$_3$Br, PPh$_3$I or (EtO)$_2$P(O), $L^2$ is a suitable leaving group such as halogen, p-toluene sulfonate, mesylate, alkoxy, and phenoxy; Pg is a suitable protecting group such as tetrahydropyranyl; and the other symbols are as defined above.

In Step 1 of FIG. 1, a Wittig reaction is carried out in a solvent such as ether, or tetrahydrofuran (THF) in the presence of a base such as sodium hydride, n-butyl lithium or lithium diisopropylamide (LDA) at 0° C. up to the reflux temperature for the solvent used for 5 minutes to 72 h. Compounds represented by Formula II in FIG. 1 can be prepared by methods disclosed in JP 61/152673, U.S. Pat. No. 5,089, 496, WO 89/10369, WO 92/20681 and WO 93/02081the entire teachings of which are incorporated herein by reference.

In Step 2 of FIG. 1, deprotection is carried out with an acid in a solvent such as methanol at room temperature up to the reflux temperature for the solvent used for 5 minutes to 72 h. Alternatively, a compound of represented by Formula V in FIG. 1 can be prepared directly from step 1 without isolating an intermediate. The reaction mixture obtained after the work up of the reaction described in step 1 can be dissolved in the solvent and reacted with the acid.

In Step 3 of FIG. 1, the hydroxy group can be converted to a leaving group by known methods. Compounds represented by Formula VI in FIG. 1 can be prepared by methods disclosed in J. Med. Chem., 1992 (35) 2074–2084 and JP 61/152673.

In Step 4 of FIG. 1, an alkylation reaction is carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide at room temperature up to the reflux temperature for the solvent used for 5 minutes to 72 h.

Figure 2:
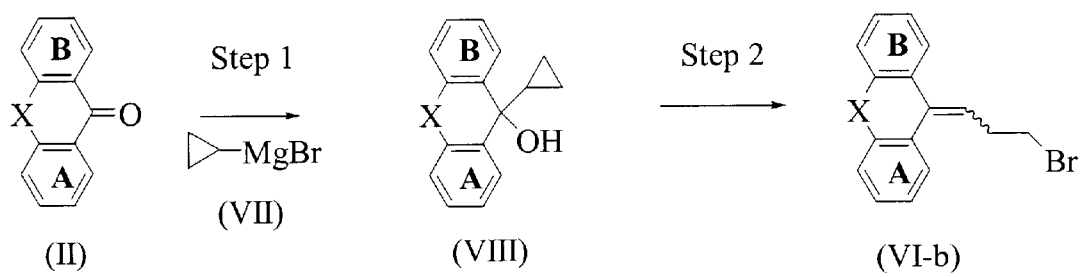
FIG. 2 is a schematic showing the preparation of the compounds represented by Compound (VI-b).

FIG. 2 shows the preparation of compounds represented by Compound (VI-b). In Step 1 of FIG. 2, a Grignard reaction may be carried out in a solvent such as ether, or tetrahydrofuran (THF) at 0° C. up to the reflux temperature for the solvent used for 5 minuets to 72 h. Compound VII is available commercially.

In Step 2 of FIG. 2, bromination may be carried out with brominate agents such as hydrobromic acid, bromotrimethylsilane or boron tribromide-methyl sulfide complex in a solvent such as acetic acid, dichloromethane or dichloroethane at room temperature up to the reflux temperature for the solvent used for 5 minutes to 72 h.

Figure 3:
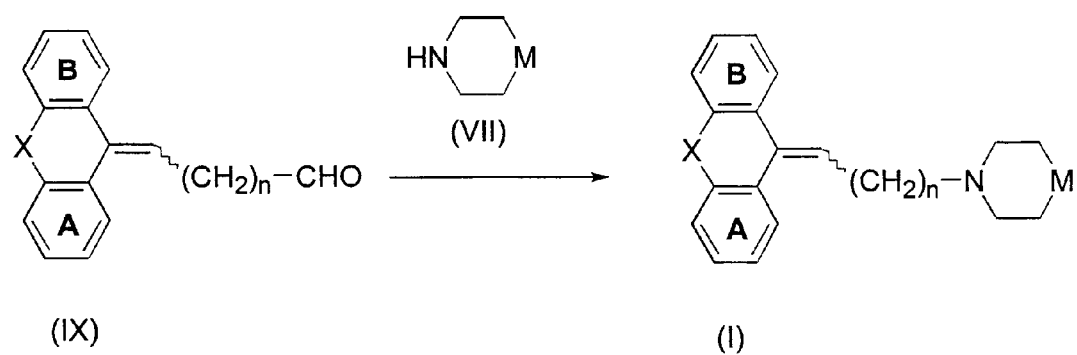
FIG. 3 is a schematic showing the preparation of the compounds represented by Structural Formula (I)

FIG. 3 shows the preparation of compounds represented by Structural Formula (I). In FIG. 3, a reductive amination may be carried out with reducing regents such as sodium cyanoborohydride, sodium acetoxyborohydride or sodium borohydride in a solvent such as methanol, ethanol, tetrahydrofuran (THF), dichloromethane or dichloroethane at room temperature up to the reflux temperature for the solvent used for 5 minutes to 72 h.

Figure 4:
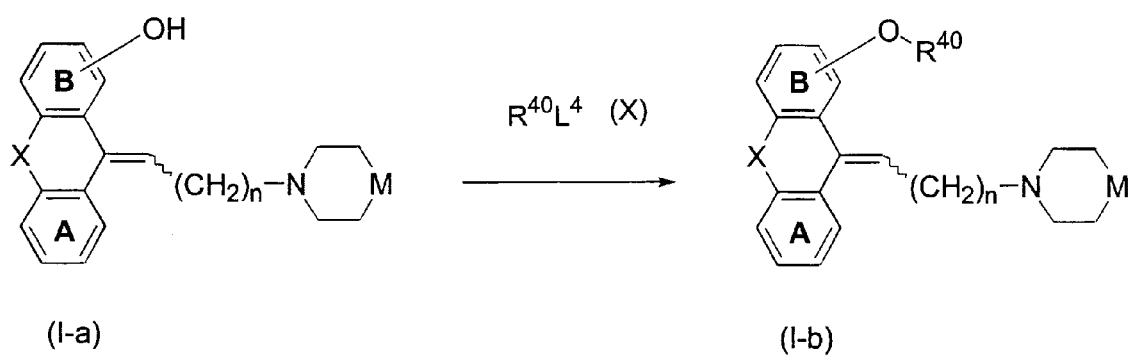
FIG. 4 is a schematic showing the preparation of the compounds represented by Structural Formula (I), wherein Z is represented by Structural Formula (III) and wherein Ring A and/or Ring B in Z is substituted with $R^{40}$.

FIG. 4 shows the preparation of compounds represented by Structural Formula (I), where in Z is represented by Structural Formulas (III) and wherein Ring A and/or Ring B in Z is substituted with $R^{40}$. In FIG. 4, an alkylation reaction may be carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide at room temperature up to the reflux temperature for the solvent used for 5 minutes to 72 h.

Figure 5:
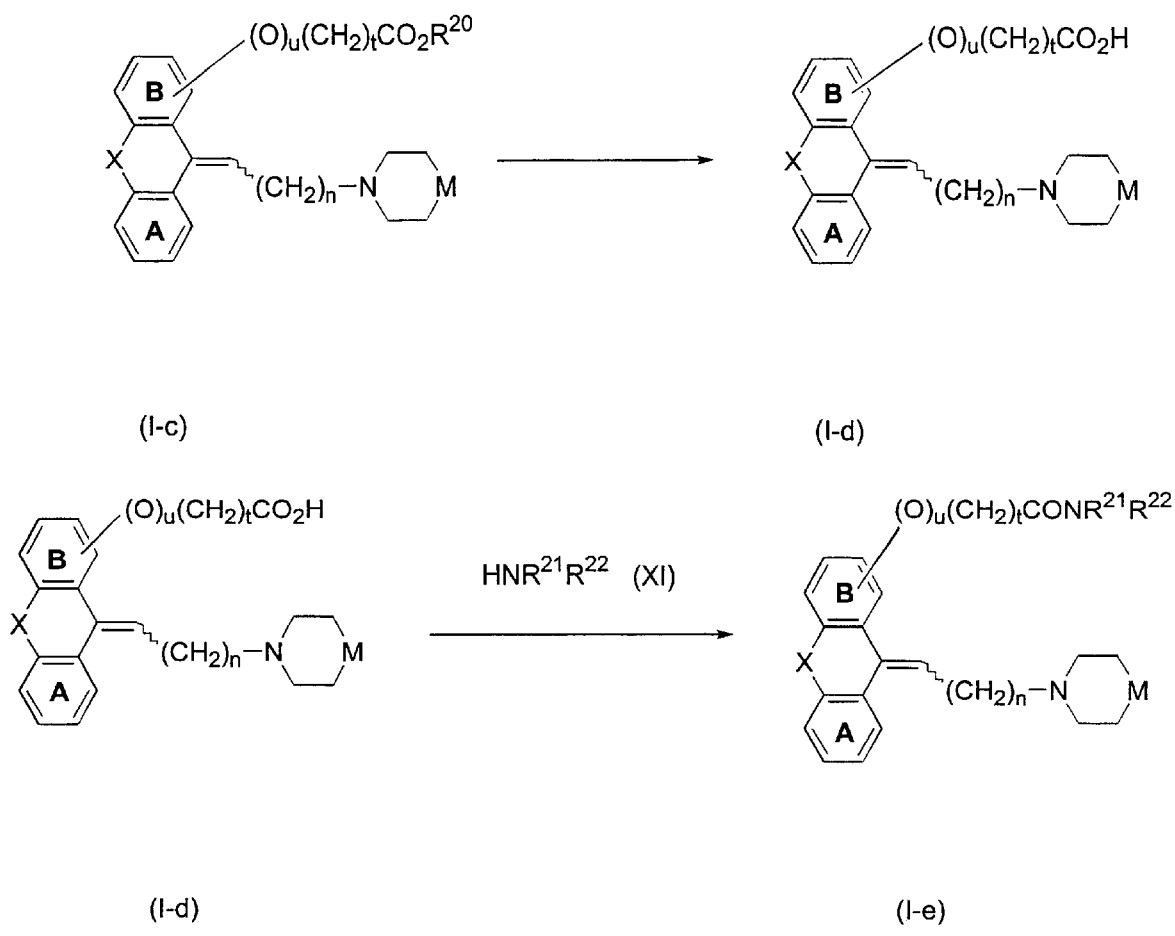
FIG. 5 is a schematic showing the preparation of the compounds represented by Structural Formula (I), wherein Z is represented by Structural Formula (III) and wherein Ring A and/or Ring B in Z is substituted with $—(O)_u—(CH_2)_t—COOR^{20}$, $—(O)_u—(CH_2)_t—C(O)—NR^{21}R^{22}$ or $—(O)_u—(CH_2)_t—NHC(O)O—R^{20}$.
Figure 6A:
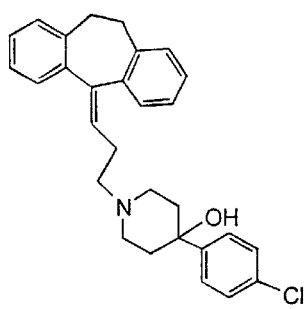
FIGS. 6A–6N show the structures of exemplary compounds of the present invention.
Figure 6A:
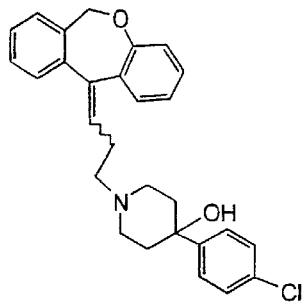
Figure 6A:
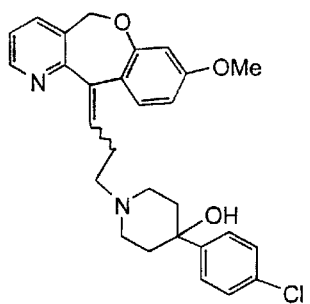
Figure 6A:
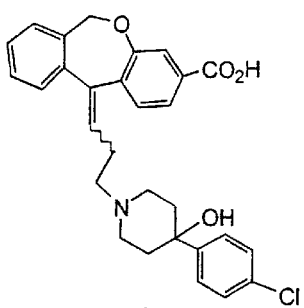
Figure 6A:
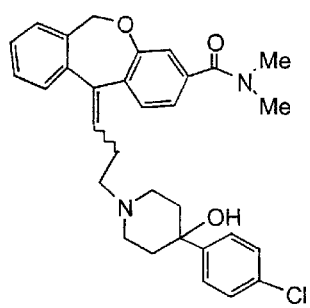
Figure 6A:
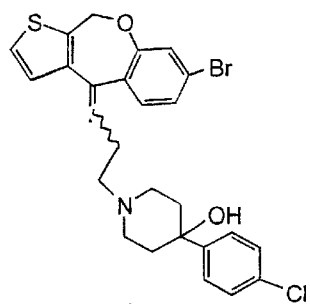
Figure 6A:
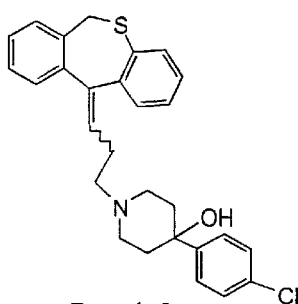
Figure 6A:
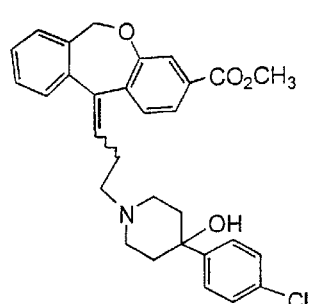
Figure 6A:
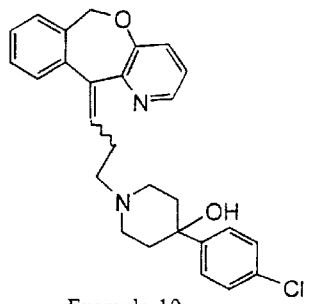
Figure 6A:
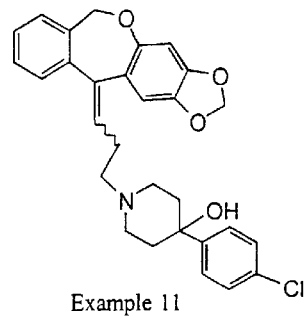
Figure 6A:
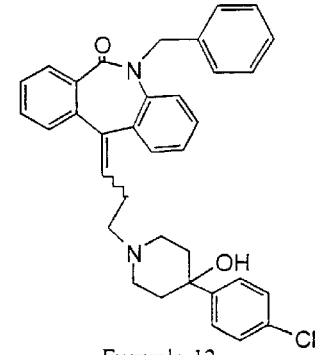
Figure 6B:
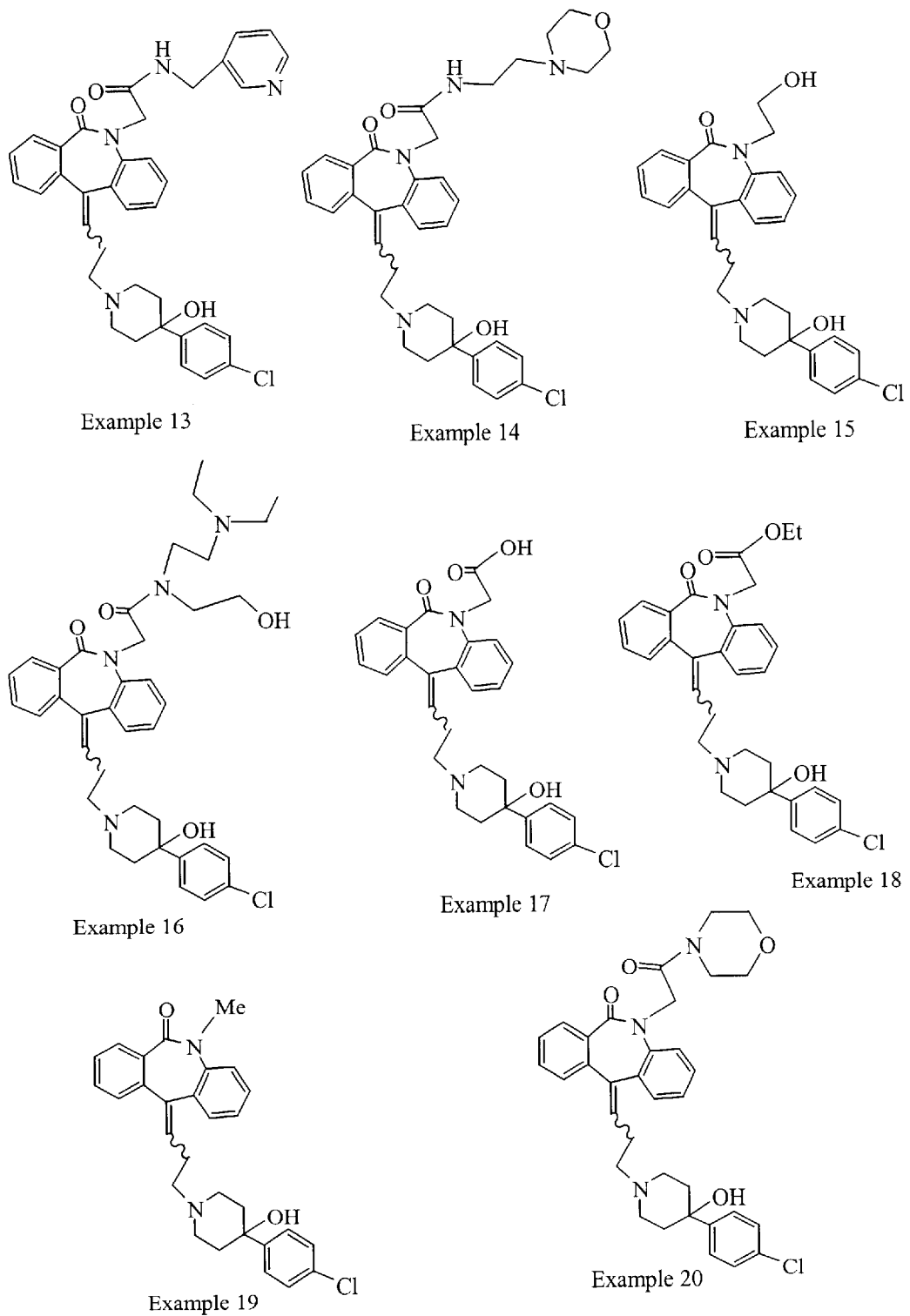
Figure 6C:
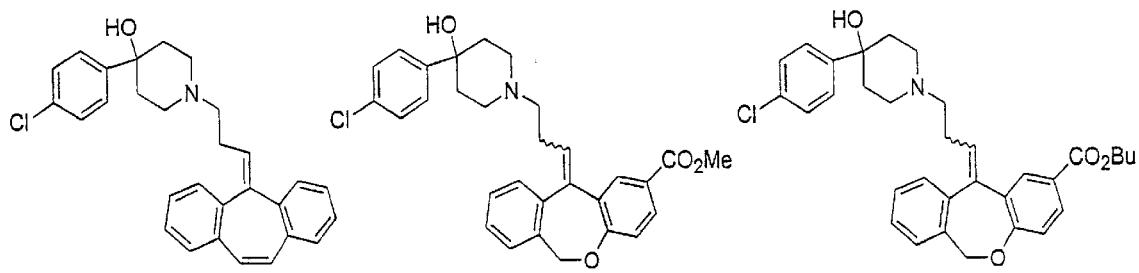
Figure 6C:
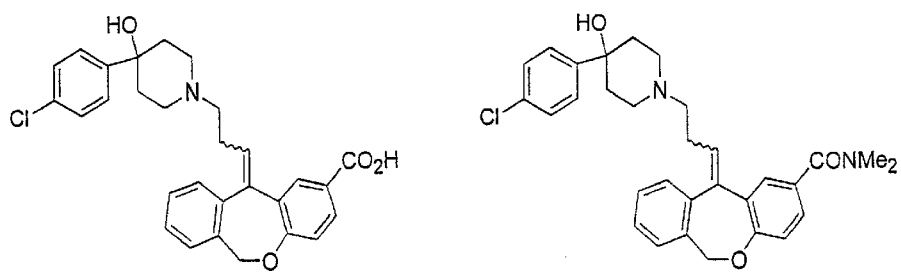
Figure 6C:
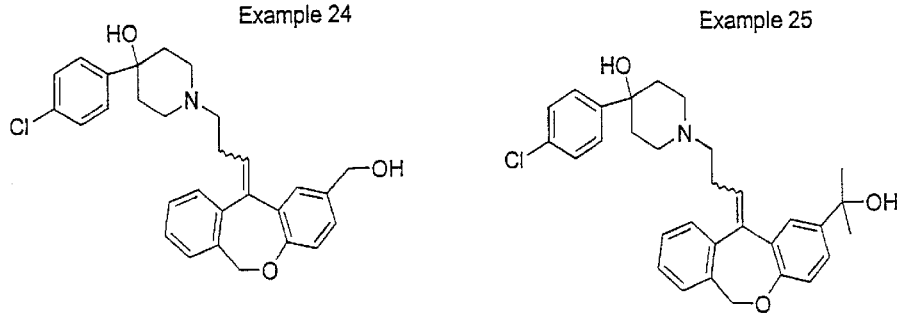
Figure 6C:
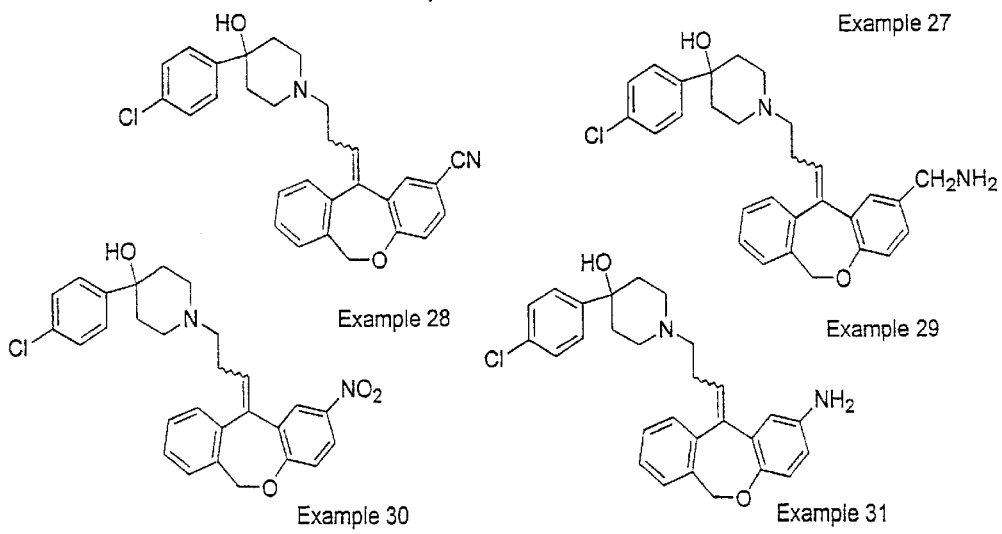
Figure 6D:
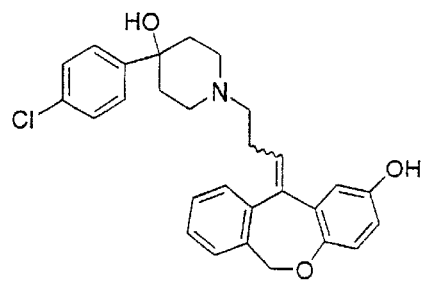
Figure 6D:
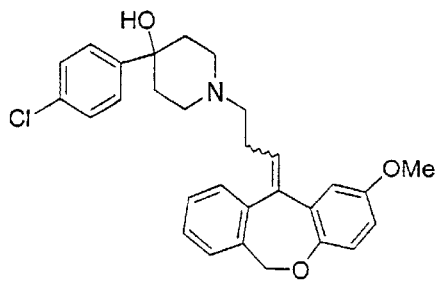
Figure 6D:
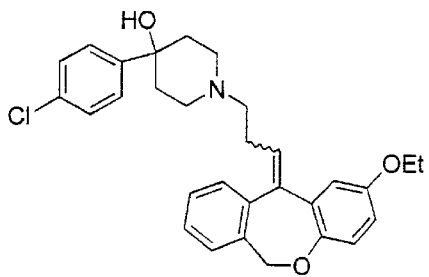
Figure 6D:
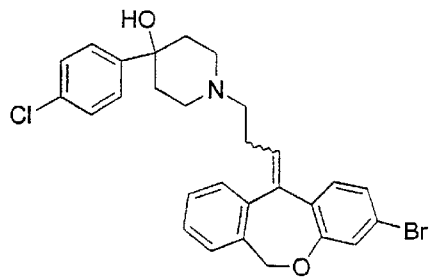
Figure 6D:
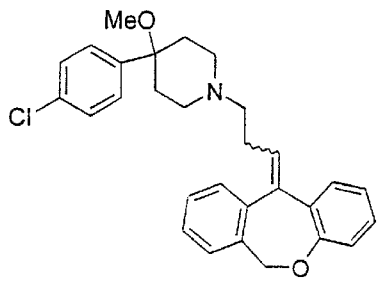
Figure 6D:
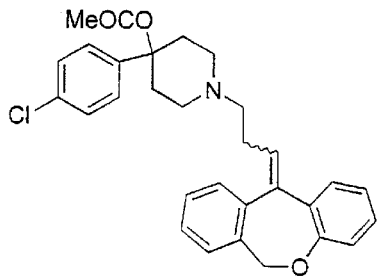
Figure 6D:
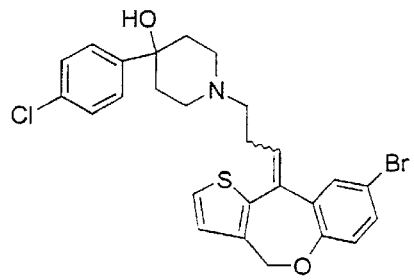
Figure 6E:
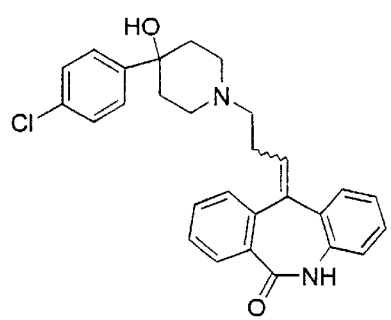
Figure 6E:
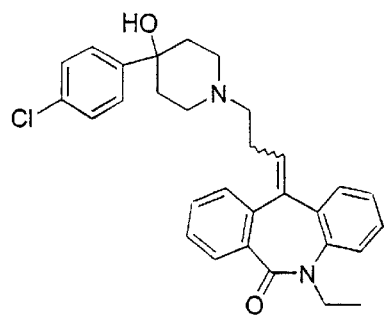
Figure 6E:
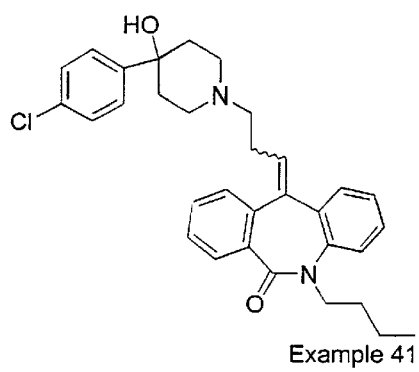
Figure 6E:
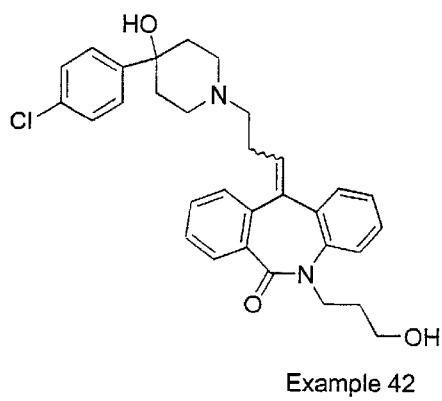
Figure 6E:
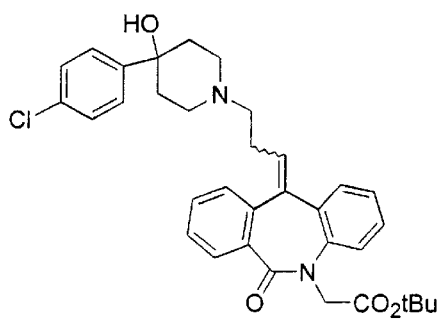
Figure 6F:
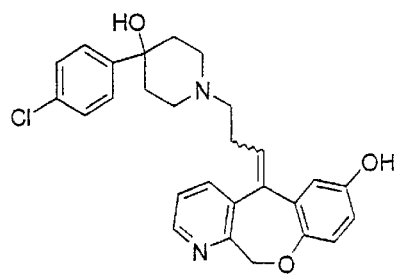
Figure 6F:
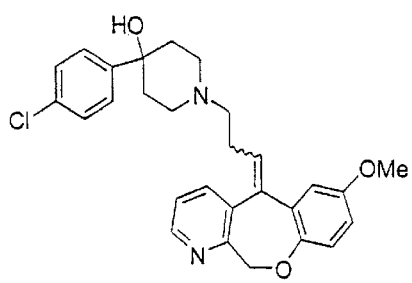
Figure 6F:
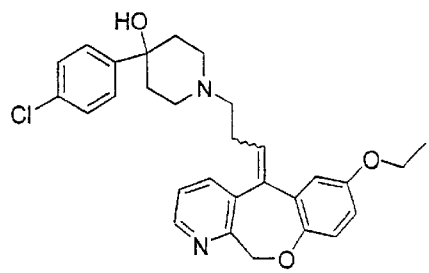
Figure 6F:
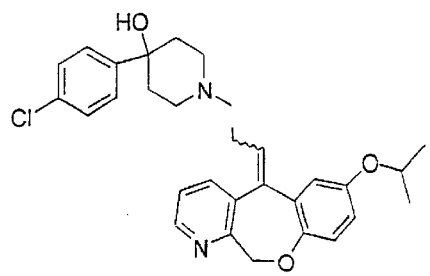
Figure 6F:
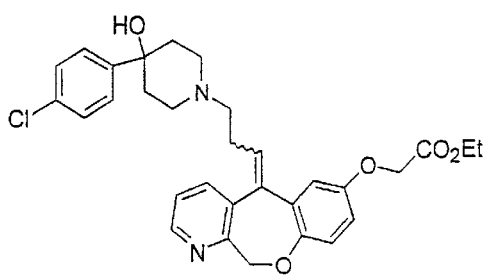
Figure 6F:
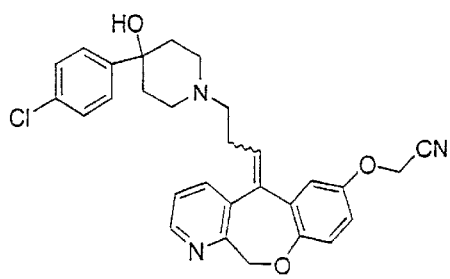
Figure 6F:
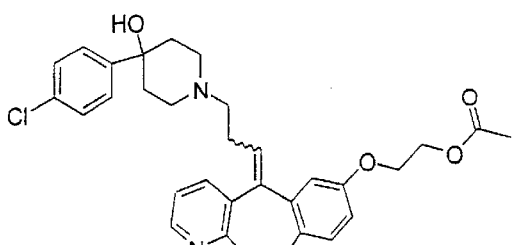
Figure 6F:
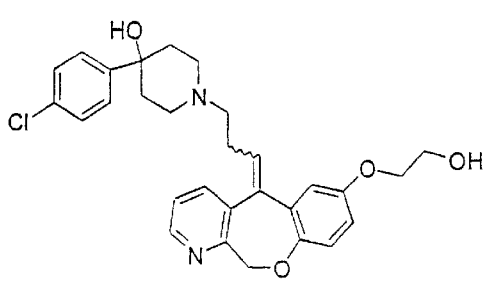
Figure 6F:
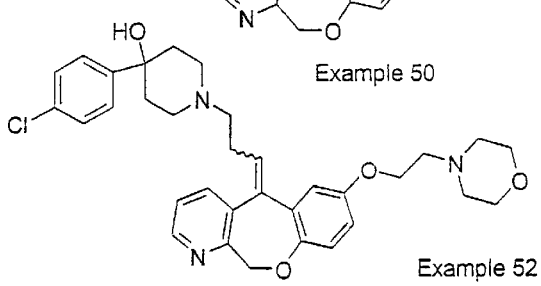
Figure 6G:
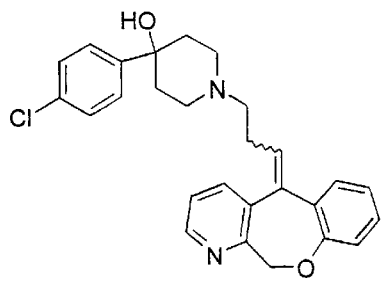
Figure 6G:
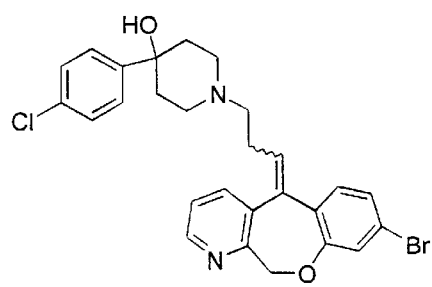
Figure 6G:
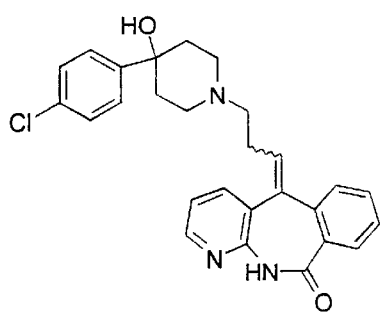
Figure 6G:
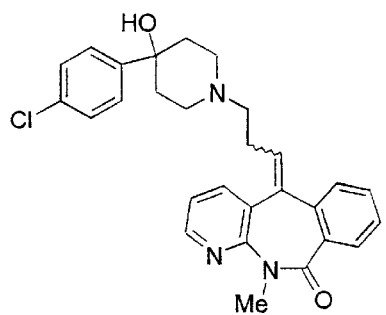
Figure 6G:
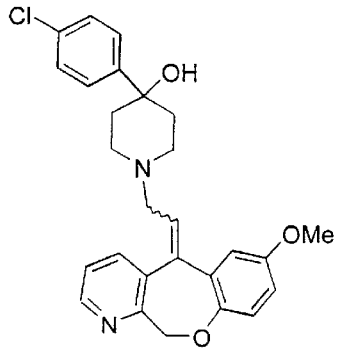
Figure 6G:
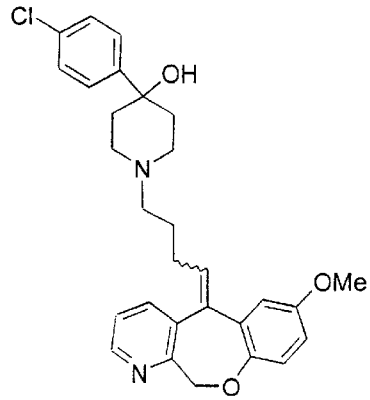
Figure 6H:
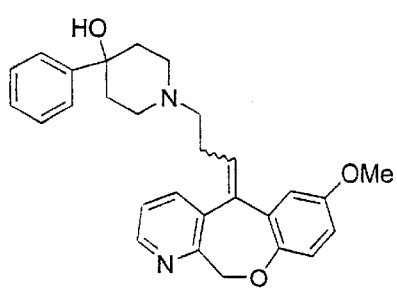
Figure 6H:
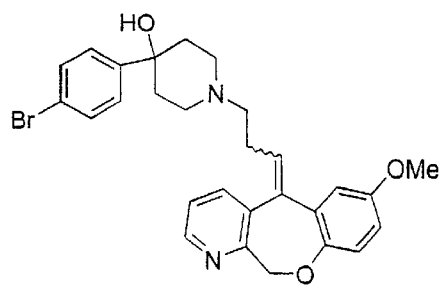
Figure 6H:
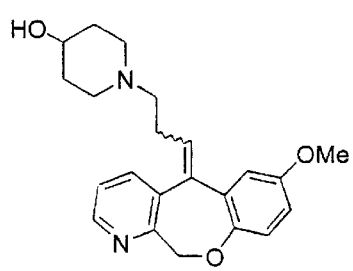
Figure 6H:
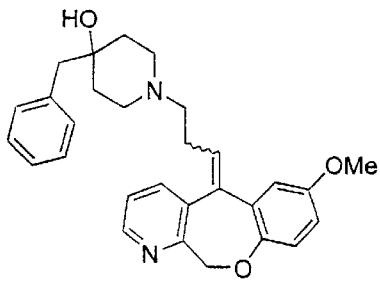
Figure 6H:
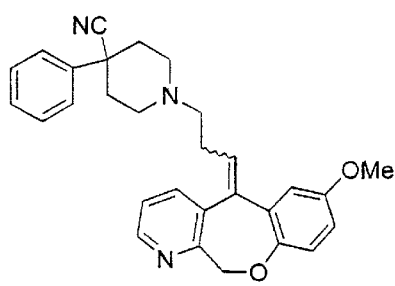
Figure 6H:
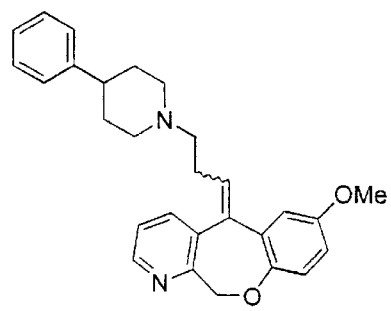
Figure 6H:
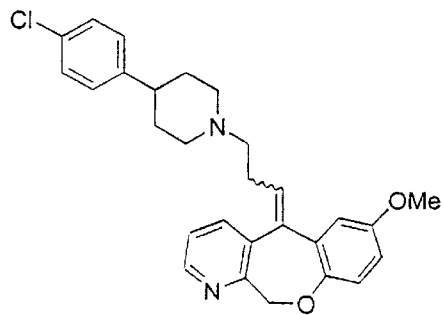
Figure 6H:
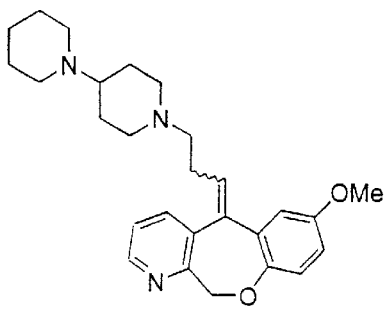
Figure 6I:
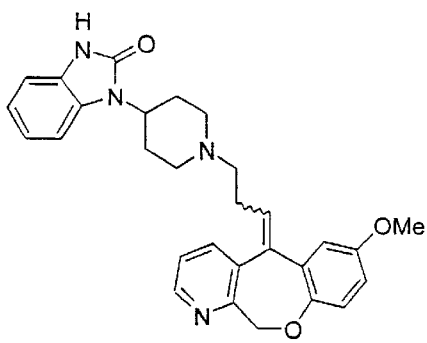
Figure 6I:
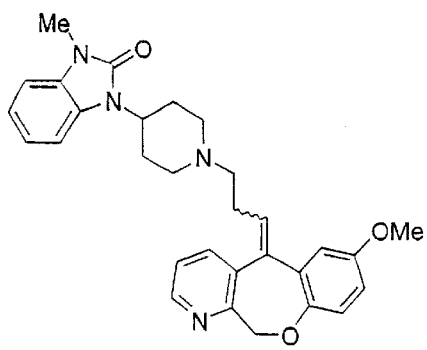
Figure 6I:
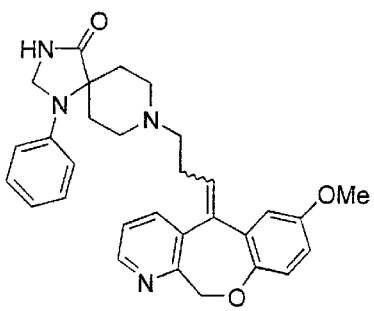
Figure 6I:
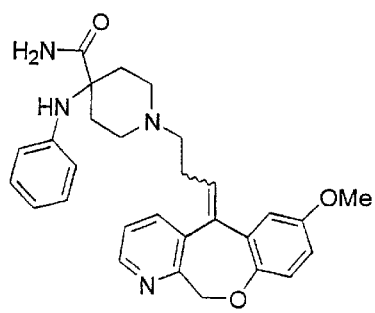
Figure 6I:
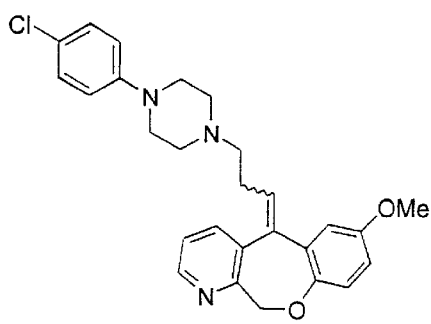
Figure 6I:
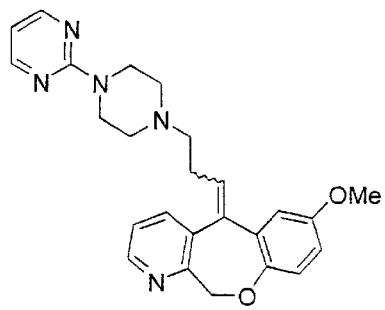
Figure 6I:
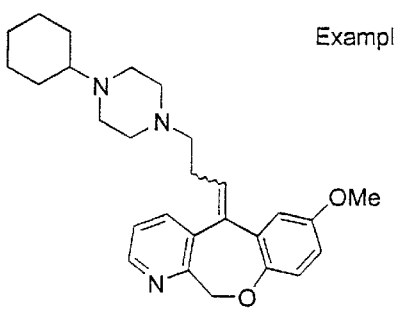
Figure 6I:
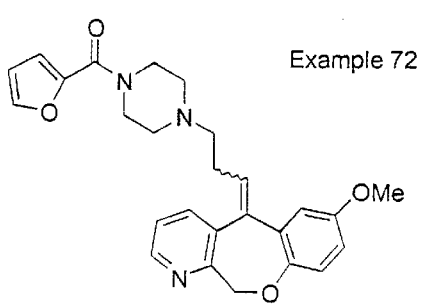
Figure 6J:
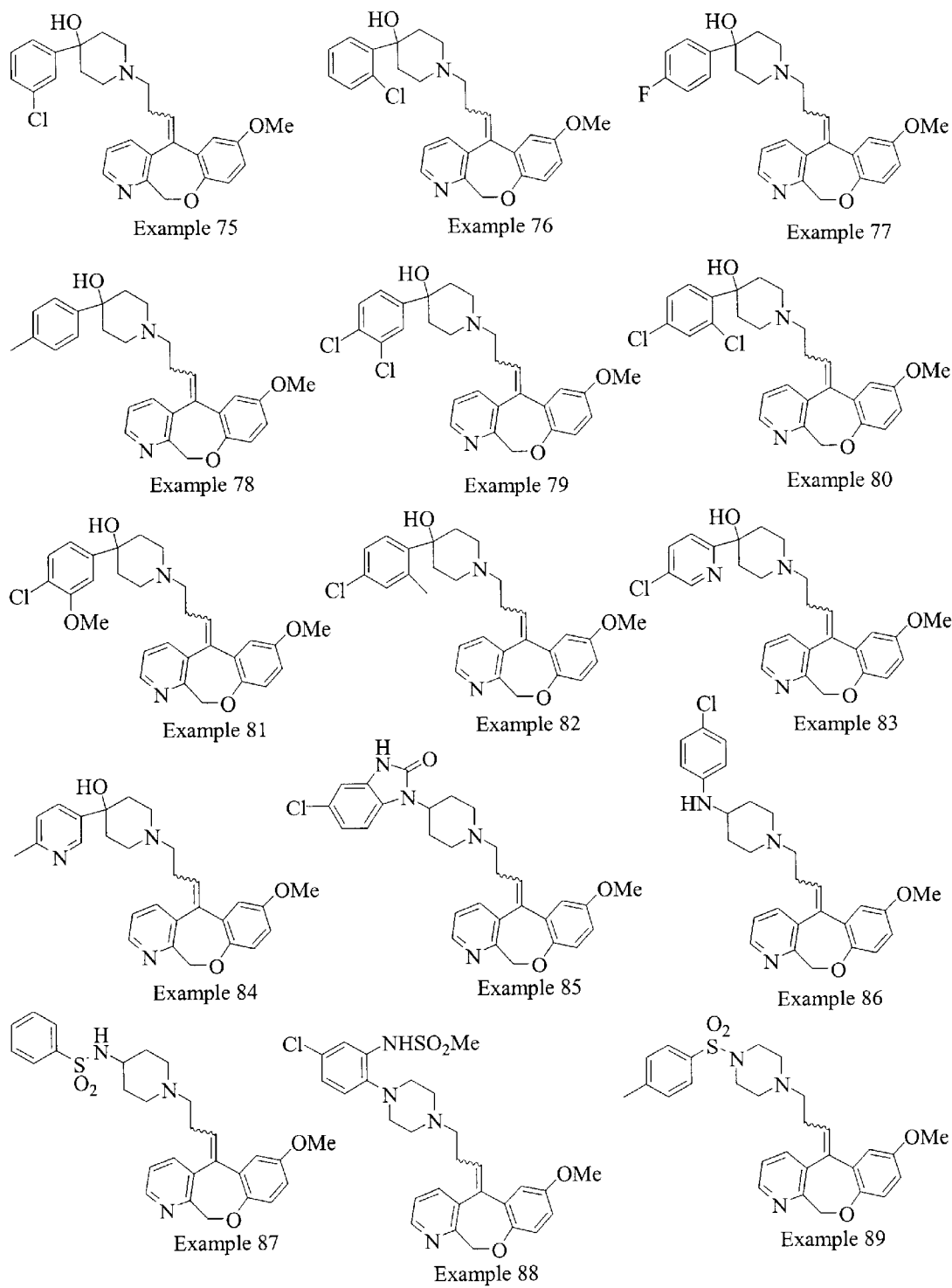
Figure 6K:
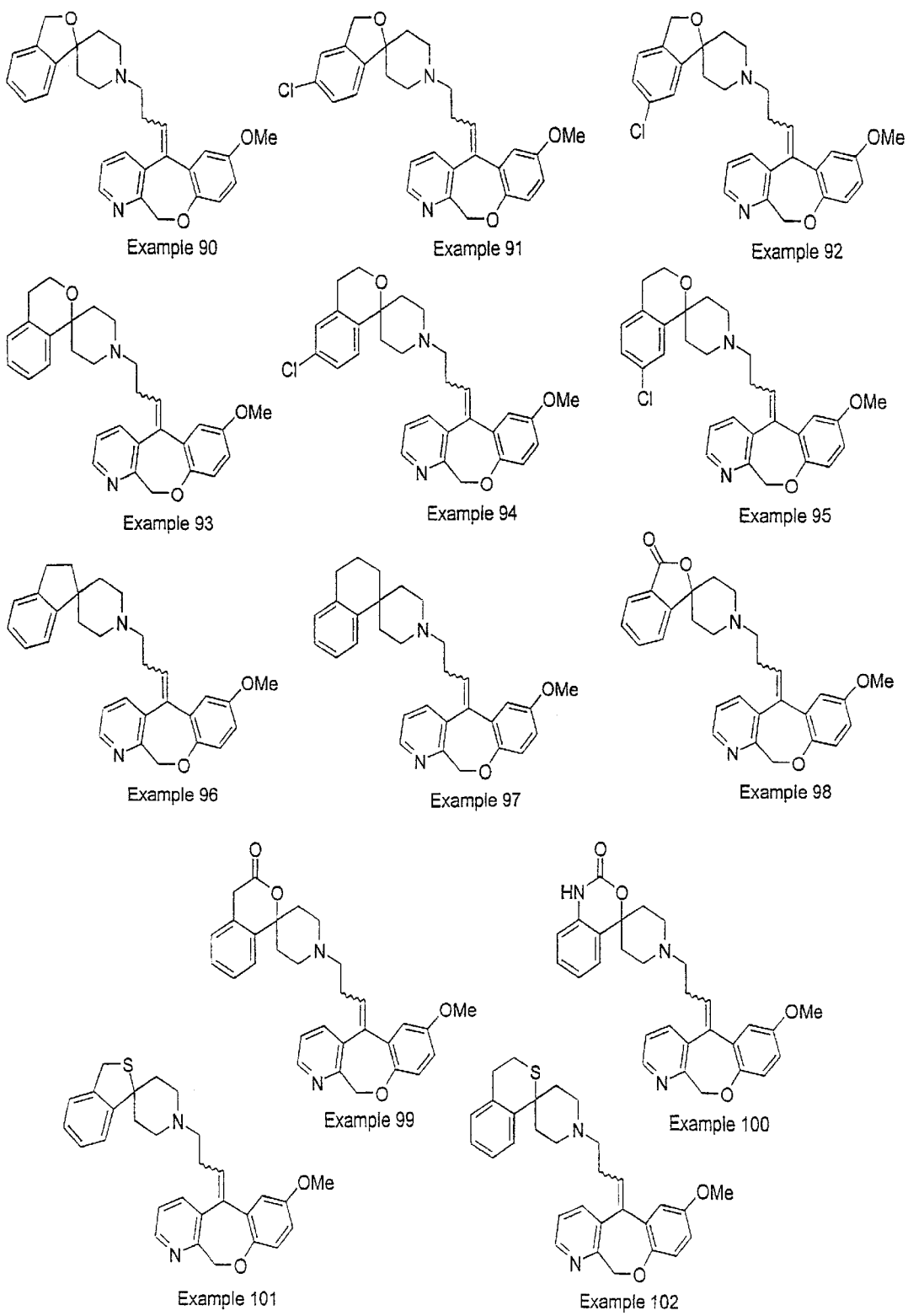
Figure 6L:
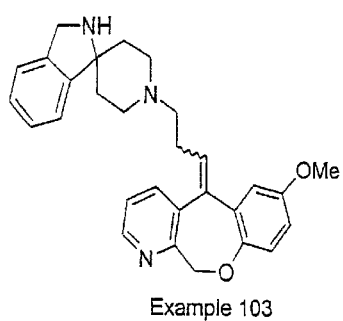
Figure 6L:
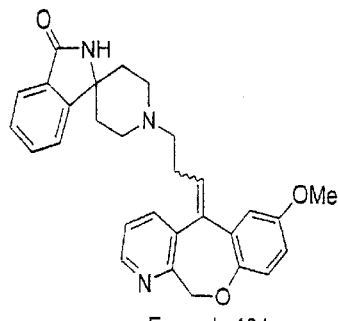
Figure 6L:
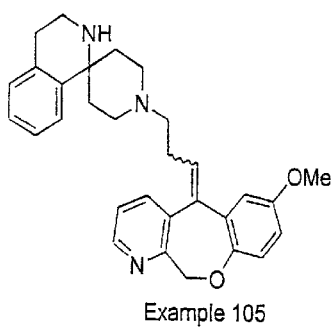
Figure 6L:
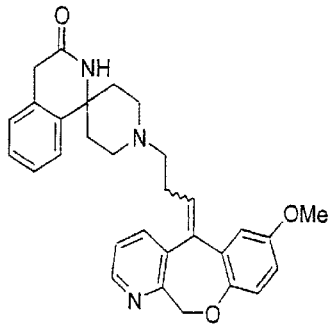
Figure 6L:
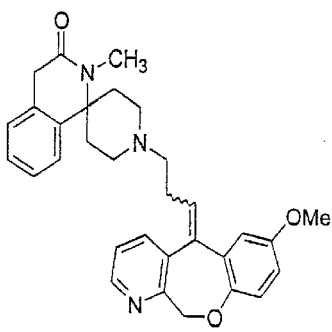
Figure 6L:
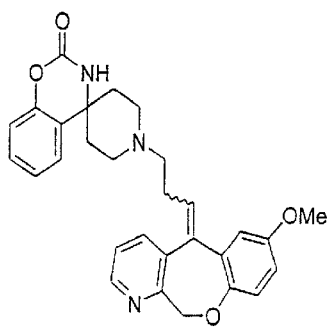
Figure 6L:
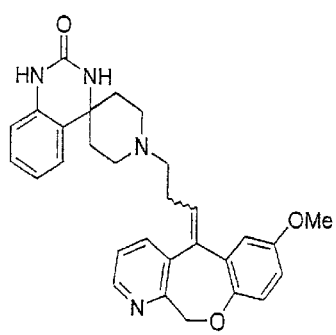
Figure 6L:
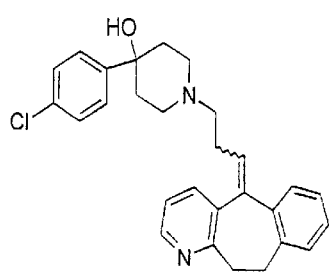
Figure 6L:
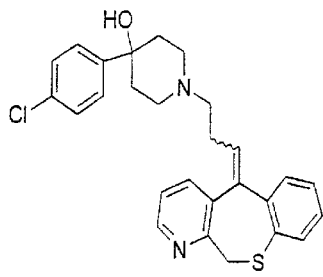
Figure 6L:
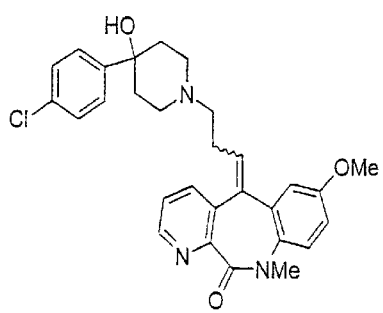
Figure 6M:
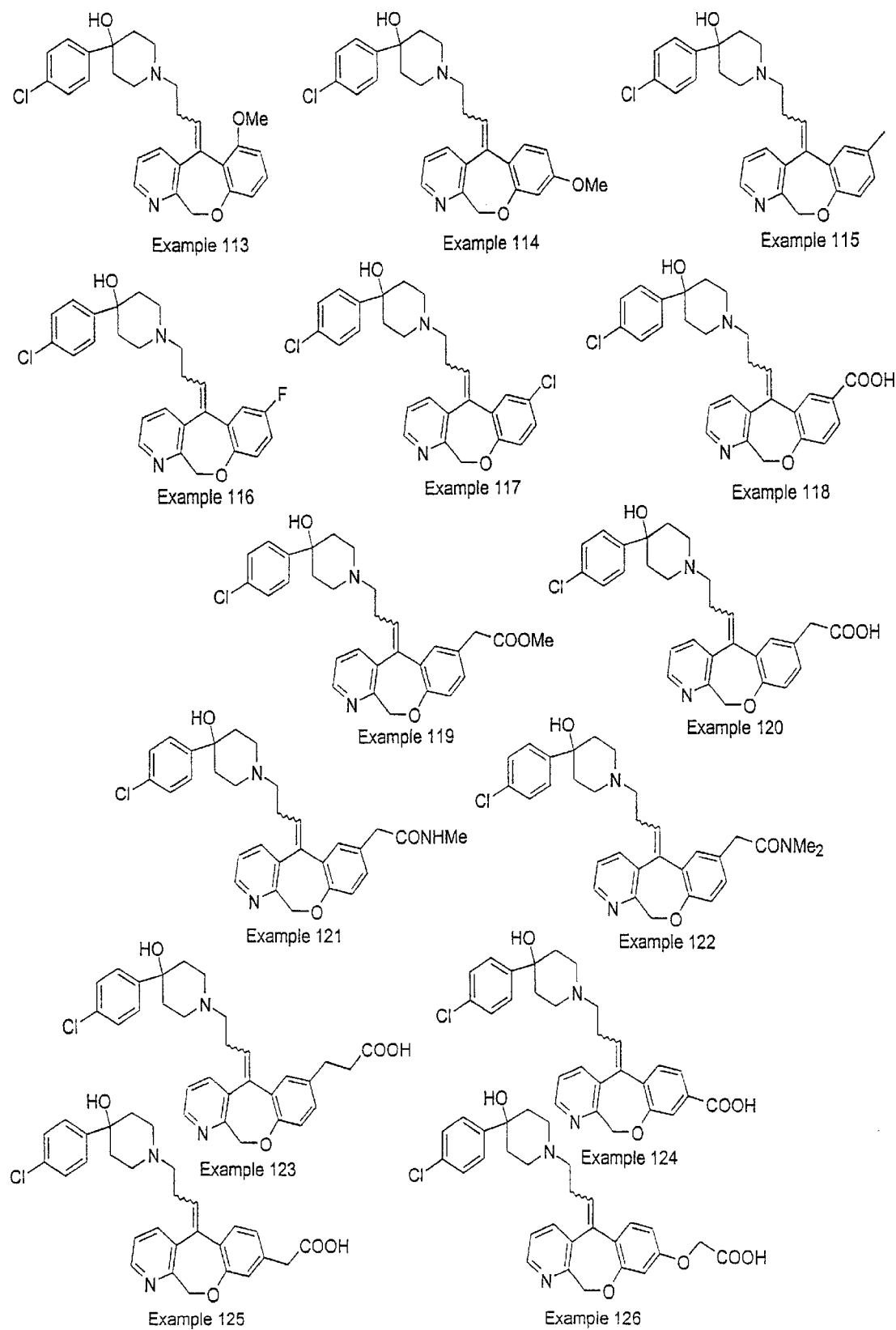
Figure 6N:
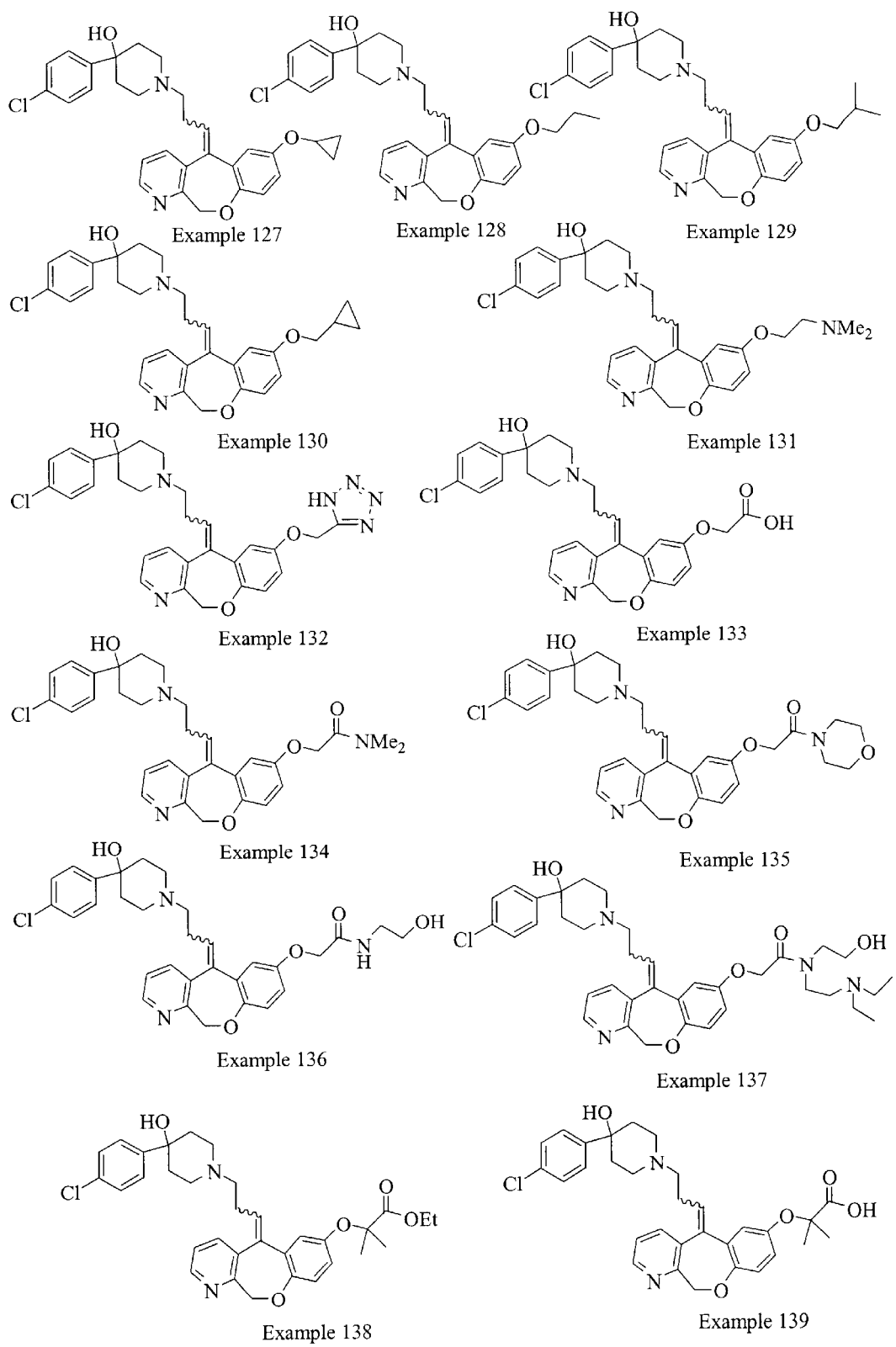

FIG. 5 is a schematic showing the preparation of the compounds represented by Structural Formula (I), wherein Z is represented by Structural Formulas (III) and wherein Ring A and/or Ring B in Z is substituted with —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)O—R$^{20}$. In FIG. 5, the hydrolysis reaction may be carried out in a mixture of aqueous alkali metal hydroxide solution and a solvent such as methanol, ethanol, tetrahydrofuran (THF) or dioxane at room temperature up to the reflux temperature for the solvent used for 5 minutes to 72 h. The acylation reaction can be carried out using dicyclohexylcarbodiimide (DCC) or (1-ethyl-3-(3-dimethylaminopropyl)carbodiimide (DEC) in a solvent such as tetrahydrofuran (THF), dimethylformamide (DMF) or methylene chloride in the presence of a base such as pyridine or triethylamine (when necessary) at temperatures of 0 to 100° C. for 5 minutes to 72 h.

Compounds represented by Structural Formula (I), wherein Z is represented by Structural Formulas (III) or (IV), X is —CO—$NR_c$— and $R_c$ is —$(CH_2)_s$—$COOR^{30}$, —$(CH_2)_s$—C(O)—$NR^{31}R^{32}$ or —$(CH_2)_s$—NHC(O)—O—$R^{30}$, can be prepared by suitable modification of the scheme shown in FIGS. 1–3. One modification utilizes the starting material shown in FIG. 1, wherein X is —CO—NH—. The amide is then alkylated with $L^3$—$(CH_2)_s$—$COOR^{30}$, wherein $L^3$ is a suitable leaving group, using the alkylation procedures described above. The remainder of the synthesis is as described in FIGS. 1–5.

Although FIGS. 1–5 show the preparation of compounds in which Rings A and B are phenyl rings, analogous compounds with heteroaryl groups for Rings A and B can be prepared by using starting materials with heteroaryl groups in the corresponding positions. These starting materials can be prepared according to methods disclosed in JP 61/152673, U.S. Pat. No. 5,089,496, WO 89/10369, WO 92/20681 and WO 93/02081.

The invention is illustrated by the following examples which are not intended to be limiting in any way.

EXEMPLIFICATION

Example 1

4-(4-Chlorophenyl)-1-[3-(10,11-dihydro-5H-dibenzo [a,d]cycloheptene-5-ylidene)propyl]piperidin-4-ol To a solution of 5-(3-bromopropylidene)-10,11-dihydro-5H-dibenzo[a,d]cycloheptene (described in JP 48-030064) (200 mg) in DMF (10 ml) were added 4-(4-chlorophenyl)-4-hydroxypiperidine (230 mg), potassium carbonate (360 mg), and potassium iodide (50 mg). The mixture was stirred at 70° C. for 24 hours. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:1) to give the titled compound (250 mg). $^1$H-NMR (CDCl$_3$) δ: 1.65–2.11 (5H, m) 2.32–3.10 (8H, m) 3.22–3.67 (4H, m), 5.87 (1H, t), 7.03–7.44 (12H, m). MS m/z: 444 (M+1).

Example 2

4-(4-Chlorophenyl)-1-[3-(6,11-dihydrodibenz[b,e] oxepin-11-ylidene)propyl]piperidin-4-ol The titled compound was prepared by following the procedure of Example 1, but replacing 5-(3-bromopropylidene)-10,11-dihydro-5H-dibenzo[a,d] cycloheptene with 11-(3-bromopropylidene)-6,11-dihydrodibenz[b,e]oxepine. $^1$H-NMR (CDCl$_3$) δ: 1.61–2.16 (5H, m), 2.37–2.80 (8H, m), 5.22 (2H, brs), 5.70 (0.6×1H, t), 6.03 (0.4×1H, t), 6.73–6.90 (2H, m), 7.09–7.45 (10H, m). MS m/z: 446 (M+1).

Example 3

Membrane Preparations for Chemokine Binding and Binding Assays

Membranes were prepared from THP-1 cells (ATCC #TIB202). Cells were harvested by centrifugation, washed twice with PBS (phosphate-buffered saline), and the cell pellets were frozen at −70 to −85° C. The frozen pellet was thawed in ice-cold lysis buffer consisting of 5 mM HEPES (N-2-hydroxyethylpiperazine-N'-2-ethane-sulfonic acid) pH 7.5, 2 mM EDTA (ethylenediaminetetraacetic acid), 5 µg/ml each aprotinin, leupeptin, and chymostatin (protease inhibitors), and 100 µg/ml PMSF (phenyl methane sulfonyl fluoride—also a protease inhibitor), at a concentration of 1 to 5×10$^7$ cells/ml. This procedure results in cell lysis. The suspension was mixed well to resuspend all of the frozen cell pellet. Nuclei and cell debris were removed by centrifugation of 400×g for 10 minutes at 4° C. The supernatant was transferred to a fresh tube and the membrane fragments were collected by centrifugation at 25,000×g for 30 minutes at 4° C. The supernatant was aspirated and the pellet was resuspended in freezing buffer consisting of 10 mM HEPES pH 7.5, 300 mM sucrose, 1 µg/ml each aprotinin, leupeptin, and chymostatin, and 10 µg/ml PMSF (approximately 0.1 ml per each 10$^8$ cells). All clumps were resolved using a minihomogenizer, and the total protein concentration was determined using a protein assay kit (Bio-Rad, Hercules, Calif., cat #500-0002). The membrane solution was then aliquoted and frozen at −70 to −85° C. until needed.

Binding Assays utilized the membranes described above. Membrane protein (2 to 20 µg total membrane protein) was incubated with 0.1 to 0.2 nM $^{125}$I-labeled RANTES or MIP-1α with or without unlabeled competitor (RANTES or MIP-1α) or various concentrations of compounds. The binding reactions were performed in 60 to 100 µl of a binding buffer consisting of 10 mM HEPES pH 7.2, 1 mM CaCl$_2$, 5 MM MgCl$_2$, and 0.5% BSA (bovine serum albumin), for 60 min at room temperature. The binding reactions were terminated by harvesting the membranes by rapid filtration through glass fiber filters (GF/B or GF/C, Packard) which were presoaked in 0.3% polyethyleneimine. The filters were rinsed with approximately 600 µl of binding buffer containing 0.5 M NaCl, dried, and the amount of bound radioactivity was determined by scintillation counting in a Topcount beta-plate counter.

The activities of test compounds are reported in the Table below as IC$_{50}$ values or the inhibitor concentration required for 50% inhibition of specific binding in receptor binding assays using $^{125}$I-RANTES or MIP-1α as ligand and THP-1 cell membranes. Specific binding is defined as the total binding minus the non-specific binding; non-specific binding is the amount of cpm still detected in the presence of excess unlabeled Rantes or $^{125}$MIP-1α.

TABLE

BIOLOGICAL DATA

| LKS-Example | IC$_{50}$ (µM) |
| --- | --- |
| 1 | <1 |
| 2 | <1 |
| 8 | <1 |
| 12 | <1 |
| 17 | <10 |
| 18 | <1 |
| 19 | <1 |
| 21 | <1 |
| 22 | <1 |
| 23 | <1 |
| 24 | <10 |
| 25 | <1 |
| 26 | <1 |
| 27 | <1 |
| 28 | <1 |

TABLE-continued

BIOLOGICAL DATA

| LKS-Example | IC$_{50}$ ($\mu$M) |
|---|---|
| 29 | <1 |
| 30 | <1 |
| 31 | <1 |
| 32 | <1 |
| 33 | <1 |
| 34 | <1 |
| 35 | <1 |
| 36 | <1 |
| 38 | <1 |
| 39 | <10 |
| 40 | <1 |
| 41 | <1 |
| 42 | <1 |
| 43 | <10 |
| 44 | <1 |
| 45 | <1 |
| 46 | <1 |
| 47 | <1 |
| 48 | <1 |
| 49 | <1 |
| 52 | <1 |
| 53 | <1 |
| 54 | <1 |
| 55 | <1 |
| 56 | <1 |
| 57 | <10 |
| 59 | <1 |
| 60 | <1 |
| 61 | <10 |
| 62 | <10 |
| 63 | <10 |
| 64 | <1 |
| 65 | <1 |
| 66 | <1000 |
| 67 | <1 |
| 68 | <10 |
| 69 | <1 |
| 71 | <1 |
| 72 | <10 |
| 73 | <10 |
| 74 | <1000 |

Example 8

4-(4-Chlorophenyl)-1-[3-(6,11-dihydrodibenz[b,e]thiepin-11-ylidene)propyl]piperidin-4-ol Step 1

11-(3-Bromopropylidene)-6,11-dihydrodibenz[b,e]thiepine was prepared by following the procedure of example 45, step 1 and 2, but replacing 5,11-dihydro-7-methoxypyrido[2,3-c][1]benzoxepin-5-one with 6,11-dihydrodibenz[b,e]thiepin-11-one.

$^1$H-NMR (CDCl$_3$) δ: 2.50–2.64 (2H, m), 3.36–3.47 (3H, m) 4.99 (1H, d), 5.94 (1H, t), 6.98–7.31 (8H, m).

Step 2

The titled compound was prepared by following the procedure of example 45, step 3 but replacing 5-(3-bromopropylidene)-10,11-dihydro-5H-dibenzo[a,d]cycloheptene with the product of step 1.

$^1$H-NMR (CDCl$_3$) δ: 1.65–1.80 (3H, m), 1.95–2.70 (10H, m), 3.35 (1H, d), 4.98 (1H, d), 5.96 (1H, t), 7.09–7.43 (12H, m). MS m/z: 462 (M+1).

Example 12

1-[3-(5-Benzyl-6,11-dihydro-6-oxo-5H-dibenz[b,e]azepin-11-ylidene)propyl]-4-(4-chlorophenyl)piperidin-4-ol To a solution 4-(4-chlorophenyl)-1-[3-(6,11-dihydro-6-oxo-5H-dibenz[b,e]azepin-11-ylidene)propyl]piperidin-4-ol hydrochloride (Example 39) (300 mg) in DMF (5 ml) were added sodium hydride (60% in oil, 200 mg), benzyl bromide (0.15 ml) and the mixture was stirred at room temperature for 1 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate to give the titled compound (180 mg).

$^1$H-NMR (CDCl$_3$) δ: 1.62–1.67 (2H, m), 1.99–2.20 (3H, m), 2.33–2.65 (8H, m), 5.10 (1H, d), 5.75 (1H, d), 5.94 (1H, t), 7.11–7.42 (16H, m), 7.91 (1H, dd). MS m/z: 549 (M+1).

Example 17

1-[3-(5-Carboxymethyl-6,11-dihydro-6-oxo-5H-dibenz[b,e]azepin-11-ylidene)propyl]-4-(4-chlorophenyl)piperidin-4-ol 4-(4-Chlorophenyl)-1-[3-(6,11-dihydro-5-ethoxycarbonymetyl-6-oxo-5H-dibenz[b,e]azepin-11-ylidene)propyl]piperidin-4-ol (Example 18) (1.0 g) was solved in 1M hydrogen chloride in diethyl ether and stirred at room temperature for 24 hours. Aqueous sodium hydroxide and ethyl acetate were added to the reaction mixture, the aqueous layer was separated and neutralized with dilute hydrochloric acid. The precipitation was filtered to give the titled compound (250 mg).

$^1$H-NMR (DMSO-d$_6$) δ: 1.44–1.61 (2H, m), 2.07–2.17 (1H, m), 2.35–3.01 (9H, m), 4.28 (1H, d), 4.59 (1H, d), 5.83 (1H, t), 7.18–7.71 (12H, m). MS m/z: 517 (M+1).

Example 18

4-(4-Chlorophenyl)-1-[3-(6,11-dihydro-5-ethoxycarbonymetyl-6-oxo-5H-dibenz[b,e]azepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-5-ethoxycarbonymetyl-6-oxo-5H-dibenz[b,e]azepine.

$^1$H-NMR (CDCl$_3$) δ: 1.30 (3H, t), 1.64–1.69 (2H, m), 1.97–2.10 (3H, m), 2.38–2.71 (8H, m), 4.27 (2H, q), 4.32 (1H, d), 4.84 (1H, d), 5.88 (1H, t), 7.16–7.45 (11H, m), 7.88 (1H, dd). MS m/z: 545 (M+1).

Example 19

4-(4-Chlorophenyl)-1-[3-(6,11-dihydro-5-methyl-6-oxo-5H-dibenz[b,e]azepin-11-ylidene)propyl]piperidin-4-ol The titled compound was prepared by following the procedure of Example 1, but replacing 5-(3-bromopropylidene)-10,11-dihydro-5H-dibenzo[a,d]cycloheptene with 11-(3-bromopropylidene)-5-methyl-6-oxo-5H-dibenz[b,e]azepin. $^1$H-NMR (CDCl$_3$) d: 1.58–2.06 (5H, m), 2.39–2.75 (8H, m), 3.53 (3H, s), 5.84 (1H, t), 7.10–7.44 (11H, m), 7.85–7.89 (1H, m). MS m/z: 473 (M+1).

Example 21

4-(4-Chlorophenyl)-1-[3-(5H-dibenzo[a,d]cycloheptene-5-ylidene)propyl]piperidin-4-ol The titled compound was prepared by following the procedure of example 1, but replacing 5-(3- bromopropylidene)-10,11-dihydro-5H-dibenzo[a,d]cycloheptene with 5-(3-bromopropylidene)-5H-dibenzo[a,d]cycloheptene.

$^1$H-NMR (CDCl$_3$) δ: 1.58–1.63 (2H, m), 2.00–2.05 (2H, m), 2.26–2.46 (6H, m), 2.62–2.66 (2H, m), 5.55 (1H, t), 6.85 (2H, s), 7.24–7.40 (12H, m). MS m/z: 442 (M+1).

Example 22

4-(4-Chlorophenyl)-1-[3-(6,11-dihydro-2-methoxycarbonyldibenz[b,e]oxepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-6,11-dihydro-2-methoxycarbonyldibenz[b,e]oxepine.

$^1$H-NMR (CDCl$_3$) δ: 1.65–1.70 (2H, m), 2.01–2.13 (3H, m), 2.41–2.80 (7H, m), 3.85 (3H, s), 5.40 (2H, brs), 5.73 (0.6×1H, t), 6.09 (0.4×1H, t), 6.76 (0.6×1H, d), 6.82 (0.4×1H, d), 7.21–7.43 (8H, m), 7.73 (1H, dd), 7.87 (0.6×1H, d), 7.97 (0.4×1H, d). MS m/z: 504 (M+1).

Example 23

1-[3-(2-Butoxycarbonyl-6,11-dihydrodibenz[b,e]oxepin-11-ylidene)propyl]-4-(4-chlorophenyl)piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-2-butoxy-6,11-dihydrodibenz[b,e]oxepine.

$^1$H-NMR (CDCl$_3$) δ: 0.96 (3H, t), 1.53 (2H, q), 1.70–1.77 (3H, m), 2.02–2.14 (3H, m), 2.39–2.78 (5H, m), 4.27 (2H, t), 5.27 (2H, brs), 5.75 (0.8×1H, t), 6.10 (0.2×1H, t), 6.78 (1H, d), 7.27–7.43 (8H, m), 7.76 (1H, dd), 7.89 (0.8×1H, d), 7.98 (0.2×1H, d). MS m/z: 546 (M+1).

Example 24

1-[3-(2-Carboxyl-6,11-dihydrodibenz[b,e]oxepin-11-ylidene)propyl]-4-(4-chlorophenyl)piperidin-4-ol To a solution of 4-(4-Chlorophenyl)-1-[3-(6,11-dihydro-2-methoxycarbonyldibenz[b,e]oxepin-11-ylidene)propyl]piperidin-4-ol (Example 22) (100 mg) in ethanol (3 ml) were added 15% sodiun hydroxide aqueous solution (0.6 ml) and the mixture was heated to reflux for 12 hours. The solvent was distilled off under reduced pressure. Water and ethyl acetate were added to the reaction mixture, the aqueous layer was separated and neutralized with dilute hydrochloric acid. The precipitation was filtered to give the titled compound (80 mg).

$^1$H-NMR (CD$_3$OD) δ: 1.73–1.79 (2H, m), 2.14–2.19 (2H, m), 2.80–2.93 (3H, m), 3.02–3.11 (3H, m), 3.24–3.29 (2H, m), 5.25 (2H, brs), 5.61 (0.7×1H, t), 6.05 (0.3×1H, t), 6.72 (1H, d), 7.22–7.40 (8H, m), 7.52–7.65 (1H, m), 7.75 (0.7×1H, d), 7.80 (0.3×1H, d). MS m/z: 490 (M+1).

Example 25

4-(4-Chlorophenyl)-1-[3-(6,11-dihydro-2-dimethylaminocarbonyldibenz[b,e]oxepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-2-dimethylaminocarbonyl-6,11-dihydrodibenz[b,e]oxepine.

$^1$H-NMR (CDCl$_3$) δ: 1.62–1.67 (2H, m), 2.00–2.12 (2H, m), 2.37–2.47 (8H, m), 2.89 (6H, s), 5.25 (2H, brs), 5.68 (0.7×1H, t), 6.03 (0.3×1H, t), 6.71 (0.3×1H, d), 6.78 (0.7×1H, d), 7.13–7.40 (10H, m). MS m/z: 517 (M+1).

Example 26

4-(4-Chlorophenyl)-1-[3-(6,11-dihydro-2-hydroxymethyldibenz[b,e]oxepin-11-ylidene)propyl]piperidin-4-ol To a solution of (4-chlorophenyl)-1-[3-(6,11-dihydromethoxycarbonyldibenz[b,e]oxepin-11-ylidene)propyl]piperidin-4-ol (110 mg) in THF (8 ml) were added lithium aluminum hydride (1.0M, 0.42 ml) dropwise at 0° C., and the mixture was stirred at room temperature for 1 hour. Aqueous sodium hydroxide (1M) was added to the reaction mixture to stir for 30 minutes, then ethyl acetate and brine was added to the mixture. The organic layer was separated and washed with saturated aqueous sodium chloride, and dried with magnesium sulfate. The solvent was distilled off under reduced pressure. The residue was purified by silica gel chromatography eluting with dichloromethane-methanol (10:1) to give the titled compound (90 mg).

$^1$H-NMR (CDCl$_3$) δ: 1.61–1.66 (2H, m), 1.98–2.03 (2H, m), 2.39–2.48 (3H, m), 2.57–2.79 (6H, m), 4.52 (2H, s), 5.20 (2H, brs), 5.66 (0.8×1H, t), 6.01 (0.2×1H, t), 6.67 (0.2×1H, d), 6.79 (0.8×1H, d), 7.06 (1H, dd), 7.15–7.37 (9H, m). MS m/z: 476 (M+1).

Example 27

4-(4-Chlorophenyl)-1-[3-(6,11-dihydro-2-(1-hydroxy-1-methyl)ethyldibenz[b,e]oxepin-11-ylidene)propyl]piperidin-4-ol To a solution of 4-(4-chlorophenyl)-1-[3-(6,11-dihydro-2-methoxycarbonyldibenz[b,e]oxepin-11-ylidene)propyl]piperidin-4-ol (60 mg) in THF (6 ml) were added methylmagnesium chloride (3.0M, 0.16 ml) dropwise at 0° C., and the mixture was stirred at room temperature for 2 hour, the reaction mixture was quenched by saturated ammonium aqueous, then ethyl acetate and water was added to the mixture. The organic layer was separated and washed with saturated aqueous sodium chloride, and dried with magnesium sulfate. The solvent was distilled off under reduced pressure. The residue was purified by silica gel chromatography eluting with ethyl acetate-methanol (95:5) to give the titled compound (20 mg).

$^1$H-NMR (CDCl$_3$) δ: 1.54 (0.7×6H, s), 1.62 (0.3×6H, s), 1.63–1.70 (2H, m), 2.03–2.10 (3H, m), 2.38–2.49 (3H, m), 2.62–2.82 (4H, m), 5.17 (2H, brs), 5.68 (0.7×1H, t), 6.05 (0.3×1H, t), 6.75 (0.3×1H, d), 6.83 (0.7×1H, d), 7.18–7.43 (10H, m). MS m/z: 504 (M+1).

Example 28

4-(4-Chlorophenyl)-1-[3-(2-cyano-6,11-dihydrodibenz[b,e]oxepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-2-cyano-6,11-dihydrodibenz[b,e]oxepine.

¹H-NMR (CDCl₃) δ: 1.67–1.72 (2H, m), 2.02–2.13 (2H, m), 2.37–2.77 (8H, m), 5.35 (2H, brs), 5.75 (0.7×1H, t), 6.07 (0.3×1H, t), 6.78 (0.3×1H, d), 6.82 (0.7×1H, d), 7.25–7.51 (10H, m). MS m/z: 471 (M+1).

Example 29

1-[3-(2-Aminomethyl-6,11-dihydrodibenz[b,e]oxepin-11-ylidene)propyl]-4-(4-chlorophenyl)piperidin-4-ol To a solution of 4-(4-chlorophenyl)-1-[3-(2-cyano-6,11-dihydrodibenz[b,e]oxepin-11-ylidene)propyl]piperidin-4-ol (380 mg) in EtOH (20 ml) were added Raney nickel (50% slurry in water, 60 mg), and the mixture was hydrogenated at 15 psi for 2 hours. The mixture was filtered through the celite and distilled off under reduced pressure. The residue was purified by silica gel chromatography eluting with dichloromethane-methanol-aqueous ammonium (95:5:1) to give the titled compound (130 mg).

¹H-NMR (CDCl₃) δ: 1.76–1.94 (3H, m), 2.18–2.34 (2H, m), 2.85–3.10 (8H, m), 3.88 (2H, s), 5.30 (2H, brs), 5.59 (1H, t), 6.78 (1H, d), 7.13–7.40 (10H, m). MS m/z: 475 (M+1).

Example 30

4-(4-Chlorophenyl)-1-[3-(6,11-dihydro-2-nitrodibenz[b,e]oxepin-11-ylidene)propyl]piperidin-4-ol The titled compound was prepared by following the procedure of example 1, but replacing 5-(3-bromopropylidene)-10,11-dihydro-5H-dibenzo[a,d]cycloheptene with 11-(3-bromopropylidene)-6,11-dihydro-2-nitrodibenz[b,e]oxepine.

¹H-NMR (CDCl₃) δ: 1.62–1.67 (2H, m), 1.80–2.12 (3H, m), 2.28–2.78 (8H, m), 5.05 (0.3×2H, brs), 5.40 (0.7×2H, brs), 5.90 (0.7×1H, t), 6.17 (0.3×1H, t), 6.82 (0.3×1H, d), 6.92 (0.7×1H), 7.28–7.41 (8H, m), 7.82 (1H, dd), 8.15 (0.7×1H, d), 8.22 (0.3×1H, d). MS m/z: 491 (M+1).

Example 31

1-[3-(2-Amino-6,11-dihydrodibenz[b,e]oxepin-11-ylidene)propyl]-4-(4-chlorophenyl)piperidin-4-ol To a solution of 4-(4-chlorophenyl)-1-[3-(6,11-dihydro-2-nitrodibenz[b,e]oxepin-11-ylidene)propyl]piperidin-4-ol (120 mg) in EtOH (15 ml) were added tin (II) chloride (190 mg), and the mixture was heated to reflux for 1 hour. The was distilled off under reduced pressure. The residue was added ethyl acetate and sodium aqueous to neutralize. The organic layer was separated and washed with saturated aqueous sodium chloride, and dried with magnesium sulfate. The solvent was distilled off under reduced pressure. The residue was purified by silica gel chromatography eluting with dichloromethane-methanol (95:5) to give the titled compound (70 mg).

¹H-NMR (DMSO-d₆) δ: 1.54–1.60 (2H, m), 1.85–2.00 (2H, m) 2.30–2.80 (8H, m), 3.88 (2H, s), 5.07 (2H, brs), 5.66 (1H, t), 6.41–6.46 (2H, m), 6.59 (1H, d), 7.24–7.49 (8H, m). MS m/z: 461 (M+1).

Example 32

4-(4-Chlorophenyl)-1-[3-(6,11-dihydro-2-hydroxydibenz[b,e]oxepin-11-ylidene)propyl]piperidin-4-ol Step 1

11-(3-Bromopropylidene)-6,11-dihydro-2-hydroxydibenz[b,e]oxepine was prepared by following the procedure of example 45, step 1 and 2, but replacing 5,11-dihydro-7-methoxypyrido[2,3-c][1]benzoxepin-5-one with 6,11-dihydro-2-hydroxydibenz[b,e]oxepin-11-one.

¹H-NMR (CDCl₃) δ: 2.69 (2H, q), 3.39 (2H, t), 5.20 (2H, brs), 5.92 (1H, t), 6.50–6.81 (4H, m), 7.17–7.37 (4H, m).

Step 2

The titled compound was prepared by following the procedure of example 45, step 3, but replacing 5-(3-bromopropylidene)-10,11-dihydro-5H-dibenzo[a,d]cycloheptene with the product of step 1.

¹H-NMR (CDCl₃) δ: 1.60–1.75 (3H, m), 1.95–2.10 (2H, m), 2.35–2.80 (8H, m), 5.10 (2H, brs), 5.93 (1H, t), 6.56 (2H, brs), 6.71 (1H, brs), 7.11–7.35 (8H, m). MS m/z: 462 (M+1).

Example 33

4-(4-Chlorophenyl)-1-[3-(6,11-dihydro-2-methoxydibenz[b,e]oxepin-11-ylidene)propyl]piperidin-4-ol Step 1

11-(3-Bromopropylidene)-6,11-dihydro-2-methoxydibenz[b,e]oxepine was prepared by following the procedure of example 45, step 1 and 2, but replacing 5,11-dihydro-7-methoxypyrido[2,3-c][1]benzoxepin-5-one with 6,11-dihydro-2-methoxydibenz[b,e]oxepin-11-one.

¹H-NMR (CDCl₃) d: 2.74 (2H, q), 3.43 (2H, t), 3.77 (3H, s), 5.10 (2H, brs), 6.02 (1H, t), 6.70–6.83 (3H, m), 7.21–7.38 (4H, m).

Step 2

The titled compound was prepared by following the procedure of example 45, step 3, but replacing 5-(3-bromopropylidene)-10,11-dihydro-5H-dibenzo[a,d]cycloheptene with the product of step 1.

¹H-NMR (CDCl₃) δ: 1.59–1.65 (2H, m), 1.95–2.66 (11H, m), 3.75 (3H, s), 5.10 (2H, brs), 6.03 (1H, t), 6.69 (2H, brs), 6.82 (1H, brs), 7.20–7.40 (8H, m). MS m/z: 476 (M+1).

Example 34

4-(4-Chlorophenyl)-1-[3-(6,11-dihydro-2-ethoxydibenz[b,e]oxepin-11-ylidene)propyl]piperidin-4-ol To a solution of 4-(4-chlorophenyl)-1-[3-(6,11-dihydro-2-hydroxydibenz[b,e]oxepin-11-ylidene)propyl]piperidin-4-ol (Example 32) (200 mg) in DMF (5 ml) were added sodium hydride (60% in oil, 25 mg), ethyl iodide (0.052 ml) and the mixture was stirred at room temperature for 1 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:1) to give the titled compound (170 mg).

¹H-NMR (CDCl₃) δ: 1.37 (3H, t), 1.60–1.65 (2H, m), 1.95–2.08 (3H, m), 2.28–75 (8H, m), 3.96 (2H, q), 5.15 (2H, brs), 6.02 (1H, t), 6.68 (2H, brs), 6.82 (1H, brs), 7.19–7.42 (8H, m). MS m/z: 490 (M+1).

Example 35

1-[3-(3-Bromo-6,11-dihydrodibenz[b,e]oxepin-11-ylidene)propyl]-4-(4-chlorophenyl)piperidin-4-ol Step 1

3-Bromo-11-(3-bromopropylidene)-6,11-dihydrodibenz[b,e]oxepine was prepared by following the procedure of example 45, step 1 and 2, but replacing 5,11-dihydro-7-methoxypyrido[2,3-c][1]benzoxepin-5-one with 3-bromo-6,11-dihydrodibenz[b,e]oxepin-11-one.

$^1$H-NMR (CDCl$_3$) δ: 2.74 (2H, q), 3.43 (2H, t), 3.77 (3H, s), 5.10 (2H, brs), 6.02 (1H, t), 6.70–6.83 (3H, m), 7.21–7.38 (4H, m).

Step 2

The titled compound was prepared by following the procedure of example 45, step 3, but replacing 5-(3-bromopropylidene)-10,11-dihydro-5H-dibenzo[a,d]cycloheptene with the product of step 1.

$^1$H-NMR (CDCl$_3$) δ: 1.63–1.70 (3H, m), 1.96–2.10 (2H, m), 2.32–2.69 (8H, m), 5.20 (2H, brs), 6.00 (1H, t), 6.92–7.00 (2H, m), 7.11–7.14 (1H, m), 7.24–7.42 (8H, m). MS m/z: 524, 526 (M+1).

Example 36

4-(4-Chlorophenyl)-1-[3-(6,11-dihydrodibenz[b,e]oxepin-11-ylidene)propyl]-4-methoxypiperidine To a solution of 4-(4-chlorophenyl)-1-[3-(6,11-dihydro-2-methoxydibenz[b,e]oxepin-11-ylidene)propyl]piperidin-4-ol (Example 2) (400 mg) in DMF (5 ml) were added sodium hydride (60% in oil, 50 mg), methyl iodide (0.07 ml) and the mixture was stirred at room temperature for 1 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:1) to give the titled compound (100 mg).

$^1$H-NMR (CDCl$_3$) δ: 1.90–2.04 (4H, m), 2.34–2.62 (8H, m), 2.93 (3H, s), 5.25 (2H, brs), 6.04 (1H, t), 6.75–6.91 (3H, m), 7.09–7.37 (9H, m). MS m/z: 460 (M+1).

Example 37

4-Acetoxy-4-(4-chlorophenyl)-1-[3-(6,11-dihydrodibenz[b,e]oxepin-11-ylidene)propyl]piperidine To a solution of 4-(4-chlorophenyl)-1-[3-(6,11-dihydro-2-methoxydibenz[b,e]oxepin-11-ylidene)propyl]piperidin-4-ol (Example 2) (200 mg) in dichloromethane (5 ml) were added acetyl chloride (0.06 ml), triethylamine (0.19 ml) and the mixture was stirred at room temperature for 1 hour. Aqueous sodium bicarbonate and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:4) to give the titled compound (190 mg).

$^1$H-NMR (CDCl$_3$) δ: 1.98–2.85 (12H, m), 2.02 (3H, s), 2.93 (3H, s), 5.23 (2H, brs), 6.01 (1H, t), 6.73–6.90 (3H, m), 7.11–7.40 (9H, m). MS m/z: 488 (M+1).

Example 38

1-[3-(8-Bromo-4,10-dihydrothieno[3,2-c][1]benzoxepin-10-ylidene)propyl]piperidin-4-(4-chlorophenyl)-4-ol Step 1

8-Bromo-10-(3-bromopropylidene)-4,10-dihydrothieno[3,2-c][1]benzoxepine was prepared by following the procedure of example 45, step 1 and 2, but replacing 5,11-dihydro-7-methoxypyrido[2,3-c][1]benzoxepin-5-one with 4,10-dihydrothieno[3,2-c][1]benzoxepin-10-one.

$^1$H-NMR (CDCl$_3$) δ: 2.84 (2H, q), 3.45 (2H, t), 5.10 (2H, s), 6.11 (1H, t), 6.65 (1H, d), 7.03–7.08 (2H, m), 7.38–7.43 (2H, m).

Step 2

The titled compound was prepared by following the procedure of example 45, step 3, but replacing 5-(3-bromopropylidene)-10,11-dihydro-5H-dibenzo[a,d]cycloheptene with the product of step 1.

$^1$H-NMR (CDCl$_3$) δ: 1.66–1.75 (3H, m), 2.03–2.16 (2H, m), 2.40–2.86 (8H, m), 5.09 (0.7×2H, s), 5.14 (0.3×2H, s), 5.90 (0.3×1H, t), 6.10 (0.7×1H, t), 6.64 (0.7×1H, d), 6.75 (0.3×1H, d), 6.90 (0.3×1H, d), 7.03–7.09 (2H, m), 7.21–7.45 (6H, m). MS m/z: 532 (M+1).

Example 39

4-(4-Chlorophenyl)-1-[3-(6,11-dihydro-6-oxo-5H-dibenz[b,e]azepin-11-ylidene)propyl]piperidin-4-ol Step 1

11-(3-Bromopropylidene)-6,11-dihydro-6-oxo-5H-dibenz[b,e]azepine was prepared by following the procedure of example 45, step 1 and 2, but replacing 5,11-dihydro-7-methoxypyrido[2,3-c][1]benzoxepin-5-one with 6,11-dihydro-6-5H-dibenz[b,e]azepin-6,11-dione.

$^1$H-NMR (CDCl$_3$) δ: 2.70–2.92 (2H, m), 3.45 (2H, t), 5.92 (1H, t), 7.08–7.58 (7H, m), 8.05 (1H, dd), 9.00 (1H, brs).

Step 2

The titled compound was prepared by following the procedure of example 45, step 3, but replacing 5-(3-bromopropylidene)-10,11-dihydro-5H-dibenzo[a,d]cycloheptene with the product of step 1.

$^1$H-NMR (CDCl$_3$) δ: 1.61–1.66 (2H, m), 1.97–2.20 (3H, m), 2.35–2.68 (8H, m), 5.80 (1H, t), 7.03–7.53 (11H, m), 8.02 (1H, dd), 9.27 (1H, brs). MS m/z: 459 (M+1).

Example 40

4-(4-Chlorophenyl)-1-[3-(6,11-dihydro-5-ethyl-6-oxo-5H-dibenz[b,e]azepin-11-ylidene)propyl]piperidin-4-ol The titled compound was prepared by following the procedure of example 12, but replacing benzyl bromide with ethyl iodide.

$^1$H-NMR (CDCl$_3$) δ: 1.19–1.28 (3H, m), 1.63–1.69 (2H, m), 1.99–2.16 (3H, m), 2.37–2.70 (8H, m), 3.77–3.85 (1H, m), 4.40–4.48 (1H, m), 5.85 (1H, t), 7.12–7.45 (11H, m), 7.85 (1H, dd). MS m/z: 487 (M+1).

Example 41

1-[3-(5-n-Butyl-6,11-dihydro-6-oxo-5H-dibenz[b,e]azepin-11-ylidene)propyl]-4-(4-chlorophenyl)piperidin-4-ol The titled compound was prepared by following the procedure of example 12, but replacing benzyl bromide with n-butyl iodide.

¹H-NMR (CDCl₃) δ: 0.90–0.98 (3H, m), 1.25–2.20 (9H, m), 2.40–2.87 (8H, m), 3.62–3.72 (1H, m), 4.52–4.64 (1H, m), 5.85 (1H, t), 7.16–7.45 (11H, m), 7.88 (1H, dd). MS m/z: 515 (M+1).

Example 42

4-(4-Chlorophenyl)-1-[3-(6,11-dihydro-5-(3-hydroxypropyl)-6-oxo-5H-dibenz[b,e]azepin-11-ylidene)propyl]piperidin-4-ol To a solution 4-(4-chlorophenyl)-1-[3-(6,11-dihydro-6-oxo-5H-dibenz[b,e]azepin-11-ylidene)propyl]piperidin-4-ol hydrochloride (Example 39) (500 mg) in DMF (8 ml) were added sodium hydride (60% in oil, 200 mg), 2-(3-bromopropoxy)tetrahydro-2H-pyran (0.5 ml) and the mixture was stirred at room temperature for 6 hours. Water and ethyl acetate were added to the reaction mixture, the organic layer was separated and washed with saturated aqueous sodium chloride, and dried with magnesium sulfate. The solvent was distilled off under reduced pressure. The residue was solved in 1M hydrogen chloride in diehyl ether and stirred at room temperature for 1 hour. Aqueous sodium bicarbonate and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate to give the titled compound (250 mg).

¹H-NMR (CDCl₃) δ: 1.25–2.87(15H, m), 3.51–3.56 (2H, m), 3.76–3.82 (1H, m), 4.81–4.87 (1H, m), 5.86 (1H, t), 7.16–7.45 (11H, m), 7.82 (1H, dd). MS m/z: 517 (M+1).

Example 43

1-[3-(5-tert-Butoxycarbonymethyl-6,11-dihydro-6-oxo-5H-dibenz[b,e]azepin-11-ylidene)propyl]-4-(4-chlorophenyl)-piperidin-4-ol The titled compound was prepared by following the procedure of example 12, but replacing benzyl bromide with tert-butyl bromoacetate.

¹H-NMR (CDCl₃) δ: 1.50 (9H, s), 1.65–1.70 (2H, m), 1.95–2.10 (3H, m), 2.42–2.75 (8H, m), 4.24 (1H, d), 4.75 (1H, d), 5.88 (1H, t), 7.16–7.46 (11H, m), 7.90 (1H, dd). MS m/z: 573 (M+1).

Example 44

4-(4-Chlorophenyl)-1-[3-(5,11-dihydro-7-hydroxypyrido[2,3-c][1]benzoxepin-5-ylidene)propyl]piperidin-4-ol Step 1

To a solution of the product of example 45, step 1 (4.3 g) in dichloroethane (100 ml) was added boron tribromide-methyl sulfide complex (19.3 g) and the mixture was heated to reflux for 3 hour. Water and ethyl acetate were added to the reaction mixture and neutralized with dilute NaOH solution. The organic layer was separated and washed with saturated aqueous sodium chloride, and dried over magnesium sulfate. The solvent was distilled off under reduced pressure. The residue was purified by silica gel chromatography eluting with ethyl acetate-hexane (1:2) to give 5-(3-bromopropylidene)-5,11-dihydro-7-hydroxypyrido[2,3-c][1]benzoxepine (3.2 g).

¹H-NMR (CDCl₃) δ: 2.72 (2H, q), 3.45 (2H, t), 5.28 (2H, brs), 6.03 (1H, t), 6.66–6.80 (3H, m), 7.26 (1H, dd), 7.58 (1H, dd), 8.51 (1H, dd).

Step 2

The titled compound was prepared by following the procedure of example 45, step 3, but replacing 5-(3-bromopropylidene)-5,11-dihydro-7-methoxypyrido[2,3-c][1]benzoxepine with the product of step 1.

¹H-NMR (DMSO-d₆) δ: 1.46–1.51 (2H, m), 1.74–1.85 (2H, m), 2.29–2.51 (8H, m), 5.15 (2H, brs), 6.07 (1H, t), 6.61–6.70 (3H, m), 7.33–7.48 (5H, m), 7.73 (1H, dd), 8.47 (1H, dd), 9.06 (1H, s). MS m/z: 463 (M+1).

Example 45

4-(4-Chlorophenyl)-1-[3-(5,11-dihydro-7-methoxypyrido[2,3-c][1]benzoxepin-5-ylidene)propyl]piperidin-4-ol Step 1

To a solution of 5,11-dihydro-7-methoxypyrido[2,3-c][1]benzoxepin-5-one (5.0 g) in THF (50 ml) was added 1.1M cyclopropylmagnesium bromide THF solution (25 ml) at 0° C. The reaction mixture was warmed to room temperature, and stirred for 30 minutes. Aqueous ammonium chloride and ethyl acetate were added to the reaction mixture, the organic layer was separated and washed with saturated aqueous sodium chloride, and dried with magnesium sulfate. The solvent was distilled off under reduced pressure. The residue was filtered and washed with ethyl acetate-hexane (1:2) to give 5-cyclopropyl-5,11-dihydro-7-methoxypyrido[2,3-c][1]benzoxepin-5-ol (5.0 g).

Step 2

To a solution of the product of step 1 (4.3 g) in acetic acid (30 ml) was added 48% aqueous HBr (25 ml) at 10° C. The reaction mixture was warmed to room temperature, and stirred for 12 hours. Water and ethyl acetate were added to the reaction mixture and neutralized with dilute NaOH solution. The organic layer was separated and washed with saturated aqueous sodium chloride, and dried over magnesium sulfate. The solvent was distilled off under reduced pressure. The residue was purified by silica gel chromatography eluting with ethyl acetate-hexane (1:4) to give 5-(3-bromopropylidene)-5,11-dihydro-7-methoxypyrido[2,3-c][1]benzoxepine (5.6 g).

¹H-NMR (CDCl₃) δ: 2.74 (2H, q), 3.46 (2H, t), 3.78 (3H, s), 5.25 (2H, brs), 6.07 (1H, t), 6.72–6.82 (3H, m), 7.21–7.42 (5H, m), 7.56 (1H, dd), 8.45 (1H, dd).

Step 3

To a solution the product of step 2 (1.1 g) in DMF (15 ml) were added 4-(4-chlorophenyl)-4-hydroxypiperidine (0.81 g) and potassium carbonate (0.53 g) and the mixture was stirred at room temperature for 3 hours. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with methylene chloride-methanol (10:1) to give the titled compound as major regioisomer (0.86 g) and minor one (0.05 g).

Major Isomer

¹H-NMR (CDCl₃) δ: 1.64–1.69 (2H, m), 1.91–2.08 (3H, m), 2.34–2.69 (8H, m), 3.77 (3H, s), 5.25 (2H, brs), 6.07 (1H, t), 6.72–6.82 (3H, m), 7.21–7.42 (5H, m), 7.56 (1H, dd), 8.45 (1H, dd). MS m/z: 477 (M+1).

Minor Isomer

¹H-NMR (CDCl₃) δ: 1.65–1.79 (3H, m), 2.01–2.13 (2H, m), 2.35–2.76 (8H, m), 3.76 (3H, s), 5.22 (2H, brs), 5.95 (1H, t), 6.72–6.80 (2H, m), 7.06 (1H, d), 7.16 (1H, dd), 7.28 (2H, d), 7.42 (2H, d), 7.66 (1H, dd), 8.39 (1H, dd). MS m/z: 477 (M+1).

Example 46

4-(4-Chlorophenyl)-1-[3-(5,11-dihydro-7-ethoxypyrido[2,3-c][1]benzoxepin-5-ylidene)propyl]piperidin-4-ol The titled compound was prepared by following the procedure of example 34, but replacing 4-(4-chlorophenyl)-1-[3-(6,11-dihydro-2-hydroxydibenz[b,e]oxepin-11-ylidene)propyl]piperidin-4-ol with 4-(4-chlorophenyl)-1-[3-(5,11-dihydro-7-hydroxypyrido[2,3-c][1]benzoxepin-5-ylidene)propyl]piperidin-4-ol (example 44).

$^1$H-NMR (CDCl$_3$) δ: 1.38 (3H, t), 1.67–1.72 (3H, m), 2.05–2.16 (2H, m), 2.40–2.80 (8H, m), 3.99 (2H, q), 5.26 (2H, brs), 6.05 (1H, t), 6.71–6.82 (3H, m), 7.23–7.43 (5H, m), 7.57 (1H, dd), 8.47 (1H, dd). MS m/z: 491 (M+1).

Example 47

4-(4-Chlorophenyl)-1-[3-(5,11-dihydro-7-isopropoxypyrido[2,3-c][1]benzoxepin-5-ylidene)propyl]piperidin-4-ol The titled compound was prepared by following the procedure of example 46, but replacing ethyl iodide with isopropyl bromide.

$^1$H-NMR (CDCl$_3$) δ: 1.30 (6H, d), 1.60–1.70 (3H, m), 1.99–2.09 (2H, m), 2.33–2.69 (8H, m), 4.37–4.48 (1H, m), 5.26 (2H, brs), 6.06 (1H, t), 6.73–6.82 (3H, m), 7.21–7.43 (5H, m), 7.55 (1H, dd), 8.47 (1H, dd). MS m/z: 505 (M+1).

Example 48

4-(4-Chlorophenyl)-1-[3-(5,11-dihydro-7-ethoxycarbonylmethyloxypyrido[2,3-c][1]benzoxepin-5-ylidene)propyl]piperidin-4-ol The titled compound was prepared by following the procedure of example 46, but replacing ethyl iodide with ethyl bromoacetate.

$^1$H-NMR (CDCl$_3$) δ: 1.28 (3H, t), 1.63–1.68 (2H, m), 1.97–2.02 (3H, m), 2.33–2.68 (8H, m), 4.24 (2H, q), 4.55 (2H, s), 5.26 (2H, brs), 6.06 (1H, t), 6.73–6.88 (3H, m), 7.21–7.42 (5H, m), 7.55 (1H, dd), 8.44 (1H, dd). MS m/z: 549 (M+1).

Example 49

4-(4-Chlorophenyl)-1-[3-(7-cyanomethyloxy-5,11-dihydropyrido[2,3-c][1]benzoxepin-5-ylidene)propyl]piperidin-4-ol The titled compound was prepared by following the procedure of example 46, but replacing ethyl iodide with bromoacetonitrile.

$^1$H-NMR (CDCl$_3$) d: 1.62–1.67 (2H, m), 1.94–2.06 (2H, m), 2.21 (1H, brs), 2.34–2.66 (8H, m), 4.70 (2H, s), 5.26 (2H, brs), 6.10 (1H, t), 6.80 (2H, brs), 6.92 (1H, brs), 7.22–7.41 (5H, m), 7.56 (1H, dd), 8.44 (1H, dd). MS m/z: 502 (M+1).

Example 50

1-[3-(7-(2-Acetoxyethyl)oxy-5,11-dihydropyrido[2,3-c][1]benzoxepin-5-ylidene)propyl]-4-(4-chlorophenyl)piperidin-4-ol The titled compound was prepared by following the procedure of example 46, but replacing ethyl iodide with 2-bromoethyl acetate.

$^1$H-NMR (CDCl$_3$) δ: 1.65–1.72 (3H, m), 1.97–2.09 (5H, m), 2.37–2.70 (8H, m), 4.11–4.14 (2H, m), 4.37–4.41 (2H, m), 5.25 (2H, brs), 6.07 (1H, t), 6.75–6.84 (3H, m), 7.23–7.43 (5H, m), 7.56 (1H, dd), 8.47 (1H, dd). MS m/z: 549 (M+1).

Example 51

4-(4-Chlorophenyl)-1-[3-(5,11-dihydro-7-(2-hydroxyethyl)oxypyrido[2,3-c][1]benzoxepin-5-ylidene)propyl]piperidin-4-ol To a solution of 1-[3-(7-(2-acetoxyethyl)oxy-5,11-pyrido[2,3-c][1]benzoxepin-5-ylidene)propyl]-4-(4-chlorophenyl) piperidin-4-ol (Example 50) (140 mg) in ethanol (5 ml) were added 15% sodiun hydroxide aqueous solution (2 ml) and the mixture was heated to reflux for 1 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with methylene chloride-methanol (10:1) to give the titled compound (120 mg).

$^1$H-NMR (CDCl$_3$) δ: 1.64–1.69 (2H, m), 1.98–2.10 (3H, m), 2.36–2.79 (8H, m), 3.89–3.94 (2H, m), 3.99–4.04 (2H, m), 5.24 (2H, brs), 6.04 (1H, t), 6.71–6.84 (3H, m), 7.23–7.41 (5H, m), 7.54 (1H, dd), 8.43 (1H, dd). MS m/z: 507 (M+1).

Example 52

4-(4-Chlorophenyl)-1-[3-(5,11-dihydro-7-(2-morpholinoethyl)oxypyrido[2,3-c][1]benzoxepin-5-ylidene)propyl]piperidin-4-ol The titled compound was prepared by following the procedure of example 46, but replacing ethyl iodide with 4-(2-chloroethyl)morpholine hydrochloride.

$^1$H-NMR (CDCl$_3$) δ: 1.62–1.67 (2H, m), 1.95–2.08 (2H, m), 2.20–2.67 (13H, m), 2.74 (2H, t), 3.67–3.71 (4H, m), 4.04 (2H, t), 5.23 (2H, brs), 6.05 (1H, t), 6.73–6.82 (3H, m), 7.20–7.41 (5H, m), 7.53 (1H, dd), 8.42 (1H, dd). MS m/z: 576 (M+1).

Example 53

4-(4-Chlorophenyl)-1-[3-(5,11-dihydropyrido[2,3-c][1]benzoxepin-5-ylidene)propyl]piperidin-4-ol Step 1

5-(3-Bromopropylidene)-5,11-dihydropyrido[2,3-c][1]benzoxepine was prepared by following the procedure of example 45, step 1 and 2, but replacing 5,11-dihydro-7-methoxypyrido[2,3-c][1]benzoxepin-5-one with 5,11-dihydropyrido[2,3-c][1]benzoxepin-5-one.

$^1$H-NMR (CDCl$_3$) δ: 2.71 (2H, q), 3.46 (2H, t), 5.33 (2H, brs), 6.04 (1H, t), 7.01–7.17 (3H, m), 7.29 (1H, dd), 7.56 (1H, dd), 8.53 (1H, dd).

Step 2

The titled compound was prepared by following the procedure of example 45, step 3, but replacing 5-(3-bromopropylidene)-5,11-dihydro-7-methoxypyrido[2,3-c][1]benzoxepine with the product of step 1.

$^1$H-NMR (CDCl$_3$) δ: 1.66–1.71 (2H, m), 2.00–2.20 (3H, m), 2.36–2.69 (8H, m), 5.34 (2H, brs), 6.10 (1H, t), 6.83–6.96 (3H, m), 7.17–7.44 (6H, m), 7.60 (1H, dd), 8.46 (1H, dd). MS m/z: 447 (M+1).

Example 54

1-[3-(8-Bromo-5,11-dihydropyrido[2,3-c][1]benzoxepin-5-ylidene)propyl]-4-(4-chlorophenyl)piperidin-4-ol Step 1

8-Bromo-5-(3-bromopropylidene)-5,11-dihydropyrido[2,3-c][1]benzoxepine was prepared by following the procedure of example 45, step 1 and 2, but replacing 5,11-dihydro-7-methoxypyrido[2,3-c][1]benzoxepin-5-one with 8-bromo-5,11-dihydropyrido[2,3-c][1]benzoxepin-5-one.

$^1$H-NMR (CDCl$_3$) δ: 2.75 (2H, q), 3.50 (2H, t), 5.38 (2H, brs), 6.08 (1H, t), 6.85–6.98 (2H, m), 7.18–7.35 (3H, m), 7.59 (1H, dd), 8.54 (1H, dd).

Step 2

The titled compound was prepared by following the procedure of example 45, step 3, but replacing 5-(3-bromopropylidene)-5,11-dihydro-7-methoxypyrido[2,3-c][1]benzoxepine with the product of step 1.

$^1$H-NMR (CDCl$_3$) δ: 1.64–1.69 (2H, m), 1.90–2.07 (3H, m), 2.30—2.67 (8H, m), 5.30 (2H, brs), 6.08 (1H, t), 7.00–7.07 (2H, m), 7.13 (1H, d), 7.25–7.42 (5H, m), 7.56 (1H, dd), 8.47 (1H, dd). MS m/z: 525, 527 (M+1).

Example 55

4-(4-Chlorophenyl)-1-[3-(10,11-dihydro-10-oxo-5H-pyrido[2,3-c][2]benzazepin-5-ylidene)propyl]piperidin-4-ol Step 1

5-(3-Bromopropylidene)-10,11-dihydro-10-oxo-5H-pyrido[2,3-c][2]benzazepine was prepared by following the procedure of example 45, step 1 and 2, but replacing 5,11-dihydro-7-methoxypyrido[2,3-c][1]benzoxepin-5-one with 10,11-dihydro-5H-pyrido[2,3-c][2]benzazepin-5,10-dione.

$^1$H-NMR (CDCl$_3$) δ: 2.75–2.90 (2H, m), 3.45 (2H, t), 5.92 (1H, t), 7.04–7.70 (5H, m), 8.10 (1H, dd), 8.48 (1H, dd), 10.00 (1H, brs).

Step 2

The titled compound was prepared by following the procedure of example 45, step 3, but replacing 5-(3-bromopropylidene)-10,11-dihydro-5H-dibenzo[a,d]cycloheptene with the product of step 1.

$^1$H-NMR (CDCl$_3$) δ: 1.64–1.69 (3H, m), 2.00–2.12 (2H, m), 2.35–2.70 (8H, m), 5.82 (1H, t), 7.08 (1H, dd), 7.23–7.62 (8H, m), 8.04 (1H, dd), 8.32 (1H, dd), 8.76 (1H, brs). MS m/z: 460 (M+1).

Example 56

4-(4-Chlorophenyl)-1-[3-(10,11-dihydro-11-methyl-10-oxo-5H-pyrido[2,3-c][2]benzazepin-5-ylidene)propyl]piperidin-4-ol The titled compound was prepared by following the procedure of example 36, but replacing of 4-(4-chlorophenyl)-1-[3-(6,11-dihydro-2-methoxydibenz[b,e]oxepin-11-ylidene)propyl]piperidin-4-ol with 5-(3-bromopropylidene)-10,11-dihydro-10-oxo-5H-pyrido[2,3-c][2]benzazepine.

$^1$H-NMR (CDCl$_3$) δ: 1.64–1.70 (3H, m), 2.00–2.10 (2H, m), 2.41–2.69 (8H, m), 3.62 (3H, s), 5.82 (1H, t), 7.07 (1H, dd), 7.25–7.54 (8H, m), 7.91 (1H, dd), 8.34 (1H, dd). MS m/z: 474 (M+1).

Example 57

4-(4-Chlorophenyl)-1-[3-(5,11-dihydro-7-methoxypyrido[2,3-c][1]benzoxepin-5-ylidene)ethyl]piperidin-4-ol Step 1

To a solution of methyltriphenylphosphonium bromide (2.2 g) in THF (20 ml) was added 1.6M n-butyl lithium hexane solution (2.9 ml) at 0° C. for 30 minutes. To the reaction mixture cooled to 0° C. was added 5,11-dihydro-7-methoxypyrido[2,3-c][1]benzoxepin-5-one (1.0 g) dropwise as THF solution (5 ml), and the mixture was warmed to room temperature, and stirred for 3 hours. Aqueous ammonium chloride and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:4) to give 5,11-dihydro-7-methoxy-5-methylenepyrido[2,3-c][1]benzoxepine (0.14 g).

Step 2

To a solution of DMF (0.54 ml) was added phosphorus oxychloride (0.41 ml) at 0° C. for 10 minutes. To the reaction mixture was added the product of step 1 (210 mg) in carbontetrachloride (5 ml) and the mixture was heated to reflux for 5 hours. Aqueous sodium bicarbonate and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with ethyl acetate-hexane (1:4) to give 3-(5,11-dihydro-7-methoxypyrido[2,3-c][1]benzoxepin-5-ylidene)acetaldehyde (130 mg).

$^1$H-NMR (CDCl$_3$) δ: 3.77 (0.7×3H, s), 3.79 (0.3×3H, s), 5.31 (2H, s), 6.46 (0.7×1H, d), 6.52 (0.3×1H, d), 6.78–7.40 (4H, m), 7.68 (0.3×1H, dd), 7.78 (0.7×1H, dd), 8.55 (0.7×1H, dd), 8.64 (0.3×1H, dd), 9.62 (0.3×1H, d), 9.79 (0.7×1H, d).

Step 3

The titled compound was prepared by following the procedure of example 58, step 2, but replacing of 3-(5,11-dihydro-7-methoxypyrido[2,3-c][1]benzoxepin-5-ylidene)propanaldehyde with product of step 2.

$^1$H-NMR (CDCl$_3$) δ: 1.64–1.82 (2H, m), 1.92–2.22 (3H, m), 2.43–2.58 (2H, m), 2.79–3.45 (6H, m), 3.68 (0.3×3H, s), 3.70 (0.7×3H, s), 5.24 (2H, brs), 6.18 (0.7×1H, t), 6.21 (0.3×1H, t), 6.72–7.42 (8H, m), 7.78 (0.3×1H, dd), 7.85 (0.7×1H, dd), 8.42 (0.7×1H, dd), 8.46 (0.3×1H, dd). MS m/z: 463 (M+1).

Example 58

4-(4-Chlorophenyl)-1-[4-(5,11-dihydro-7-methoxypyrido[2,3-c][1]benzoxepin-5-ylidene)butyl]piperidin-4-ol Step 1

3-(5,11-Dihydro-7-methoxypyrido[2,3-c][1]benzoxepin-5-ylidene)propenaldehyde was prepared by following the procedure of example 57, step 2, but replacing 5,11-dihydro-7-methoxy-5-methylenepyrido[2,3-c][1]benzoxepine with 5,11-dihydro-7-methoxy-5-(propyl-1-ene)pyrido[2,3-c][1]benzoxepine (by-product of example 45, step 3).

$^1$H-NMR (CDCl$_3$) δ: 3.78 (0.3×3H, s), 3.80 (0.7×3H, s), 5.32 (2H, brs), 6.34–6.39 (1H, m), 6.72–7.38 (6H, m), 7.58

(0.7×1H, dd), 7.77 (0.3×1H, dd), 8.49 (0.3×1H, dd), 8.60 (0.7×1H, dd), 9.51 (0.7×1H, d), 9.54 (0.3×1H, d).

Step 2

To a solution of the product of step 1 (90 mg) in dichloromethane (6 ml) were added sodium triacetoxyborohydride (170 mg), 4-(4-chlorophenyl)-4-hydroxypiperidine (70 mg) and acetic acid (0.02 ml) and the mixture stirred at room temperature for 24 hour. Water and ethyl acetate were added to the reaction mixture, the organic layer was separated and washed with saturated aqueous sodium chloride, and dried with magnesium sulfate. The solvent was distilled off under reduced pressure. The residue was purified by silica gel chromatography eluting with dichloromethane-methanol (95:5) to give 4-(4-chlorophenyl)-1-[4-(5,11-dihydro-7-methoxypyrido[2,3-c][1]benzoxepin-5-ylidene) buten-2-yl]piperidin-4-ol (110 mg).

$^1$H-NMR (CDCl$_3$) δ: 1.68–1.73 (2H, m), 2.04–2.16 (2H, m), 2.43–2.72 (3H, m), 2.77–2.81 (2H, m), 3.08–3.13 (2H, m), 3.73 (0.3×3H, s), 3.77 (0.7×3H, s), 5.20 (2H, brs), 5.98–6.05 (1H, m), 6.23–7.43 (10H, m), 7.58 (0.7×1H, dd), 7.65 (0.3×1H, dd), 8.37 (0.3×1H, dd), 8.45 (0.7×1H, dd). MS m/z: 489 (M+1).

Step 3

To a solution of the product of step 2 (8 mg) in ethanol (2 ml) were added 10% Pd—C (2 mg) was stirred under hydrogen (under a balloon) at room temperature for 1 hour. The mixture was filtered through the celite and distilled off under reduced pressure to give the titled compound (6 mg).

$^1$H-NMR (CDCl$_3$) δ: 1.65–1.79 (3H, m), 2.01–2.13 (4H, m), 2.35–2.76 (8H, m), 3.76 (3H, s), 5.22 (2H, brs), 5.95 (1H, t), 6.72–6.80 (2H, m), 7.06 (1H, d), 7.16 (1H, dd), 7.28 (2H, d), 7.42 (2H, d), 7.66 (1H, dd), 8.39 (1H, dd). MS m/z: 491 (M+1).

Example 59

1-[3-(5,11-Dihydro-7-methoxypyrido[2,3-c][1] benzoxepin-5-ylidene)propyl]piperidin-4-phenyl-4-ol The titled compound was prepared by following the procedure of example 45, step 3, but replacing 4-(4-chlorophenyl)-4-hydroxypiperidine with 4-phenyl-4-hydroxypiperidine.

$^1$H-NMR (CDCl$_3$) d: 1.68–1.73 (2H, m), 2.02–2.15 (3H, m), 2.38–2.72 (8H, m), 3.77 (3H, s), 5.26 (2H, brs), 6.08 (1H, t), 6.72–6.83 (3H, m), 7.21–7.36 (4H, m), 7.46–7.49 (2H, m), 7.58 (1H, dd), 8.46 (1H, dd). MS m/z: 443 (M+1).

Example 60

4-(4-Bromophenyl)-1-[3-(5,11-dihydro-7-methoxypyrido[2,3-c][1]benzoxepin-5-ylidene) propyl]piperidin-4-ol The titled compound was prepared by following the procedure of example 45, step 3, but replacing 4-(4-chlorophenyl)-4-hydroxypiperidine with 4-(4-bromophenyl)-4-hydroxypiperidine.

$^1$H-NMR (CDCl$_3$) δ: 1.65–1.69 (2H, m), 2.00–2.10 (3H, m), 2.37–2.71 (8H, m), 3.76 (3H, s), 5.24 (2H, brs), 6.05 (1H, t), 6.70–6.82 (3H, m), 7.24 (1H, dd), 7.38 (2H, d), 7.44 (2H, s), 7.52 (1H, dd), 8.44 (1H, dd). MS m/z: 521,523 (M+1).

Example 61

1-[3-(5,11-Dihydro-7-methoxypyrido[2,3-c][1] benzoxepin-5-ylidene)propyl]piperidin-4-ol The titled compound was prepared by following the procedure of example 45, step 3, but replacing 4-(4-chlorophenyl)-4-hydroxypiperidine with 4-hydroxypiperidine.

$^1$H-NMR (CDCl$_3$) δ: 1.43–1.60 (2H, m), 1.80–1.98 (2H, m), 2.00–2.18 (3H, m), 2.34–2.48 (4H, m), 2.63–2.76 (2H, m), 3.64–3.73 (1H, m), 3.70 (3H, s), 5.35 (2H, brs), 6.06 (1H, t), 6.74–6.84 (3H, m), 7.25 (1H, dd), 7.60 (1H, dd), 8.50 (1H, dd). MS m/z: 367 (M+1).

Example 62

4-Benzyl-1-[3-(5,11-dihydro-7-methoxypyrido[2,3-c][1]benzoxepin-5-ylidene)propyl]piperidin-4-ol The titled compound was prepared by following the procedure of example 45, step 3, but replacing 4-(4-chlorophenyl)-4-hydroxypiperidine with 4-benzyl-4-hydroxypiperidine.

$^1$H-NMR (CDCl$_3$) δ: 1.42–1.57 (3H, m), 1.62–1.75 (2H, m), 2.22–2.70 (8H, m), 2.79 (2H, s), 3.80 (3H, s), 5.25 (2H, brs), 6.08 (1H, t), 6.73–6.84 (3H, m), 7.18–7.24 (6H, m), 7.57 (1H, dd), 8.50 (1H, dd). MS m/z: 457 (M+1).

Example 63

4-Cyano-1-[3-(5,11-dihydro-7-methoxypyrido[2,3-c] [1]benzoxepin-5-ylidene)propyl]-4-phenylpiperidine The titled compound was prepared by following the procedure of example 45, step 3, but replacing 4-(4-chlorophenyl)-4-hydroxypiperidine with 4-cyano-4-phenylpiperidine.

$^1$H-NMR (CDCl$_3$) δ: 1.97–2.06 (4H, m), 2.37–2.60 (6H, m), 2.85–2.90 (2H, m), 3.79 (3H, s), 5.27 (2H, brs), 6.08 (1H, t), 6.72–6.84 (3H, m), 7.24–7.58 (7H, m), 8.49 (1H, dd). MS m/z: 452 (M+1).

Example 64

1-[3-(5,11-Dihydro-7-methoxypyrido[2,3-c][1] benzoxepin-5-ylidene)propyl]-4-phenylpiperidine The titled compound was prepared by following the procedure of example 45, step 3, but replacing 4-(4-chlorophenyl)-4-hydroxypiperidine with 4-phenylpiperidine.

$^1$H-NMR (CDCl$_3$) δ: 1.73–1.79 (4H, m), 1.96–2.03 (2H, m), 2.37–2.52 (5H, m), 2.86–2.94 (2H, m), 3.77 (3H, s), 5.26 (2H, brs). 6.08 (1H, t), 6.72–6.83 (3H, m), 7.17–7.31 (6H, m), 7.56 (1H, dd), 8.49 (1H, dd). MS m/z 426 (M+1).

Example 65

4-(4-Chlorophenyl)-1-[3-(5,11-dihydro-7-methoxypyrido[2,3-c][1]benzoxepin-5-ylidene) propyl]piperidine The titled compound was prepared by following the procedure of example 45, step 3, but replacing 4-(4-chlorophenyl)-4-hydroxypiperidine with 4-(4-chlorophenyl) piperidine.

$^1$H-NMR (CDCl$_3$) δ: 1.68–1.74 (4H, m), 1.96–2.03 (2H, m), 2.36–2.48 (5H, m), 2.89–2.94 (2H, m), 3.77 (3H, s), 5.27 (2H, brs), 6.07 (1H, t), 6.73–6.83 (3H, m), 7.10–7.27 (5H, m), 7.57 (1H, dd), 8.48 (1H, dd). MS m/z: 461 (M+1).

Example 66

1-[3-(5,11-Dihydro-7-methoxypyrido[2,3-c][1] benzoxepin-5-ylidene)propyl]-4-piperidinopiperidine The titled compound was prepared by following the procedure of example 45, step 3, but replacing 4-(4- chlorophenyl)-4-hydroxypiperidine with 4-piperidinopiperidine.

$^1$H-NMR (CDCl$_3$) δ: 1.40–2.00 (12H, m), 2.15–2.60 (9H, m), 2.80–2.92 (2H, m), 3.80 (3H, s), 5.28 (2H, brs), 6.05 (1H, t), 6.75–6.86 (3H, m), 7.30 (1H, dd), 7.55 (1H, dd), 8.46 (1H, dd). MS m/z 434 (M+1).

Example 67

1-[3-(5,11-Dihydro-7-methoxypyrido[2,3-c][1]
benzoxepin-5-ylidene)propyl]-4-(2-keto-1-
imidazolinyl)piperidine The titled compound was prepared by following the procedure of example 45, step 3, but replacing 4-(4-chlorophenyl)-4-hydroxypiperidine with 4-(2-keto-1-imidazolinyl)piperidine $^1$H-NMR (CDCl$_3$) δ: 1.75–1.79 (2H, m), 2.03–2.15 (2H, m), 2.38–2.52 (6H, m), 2.93–2.98 (2H, m), 3.78 (3H, s), 4.30–4.38 (1H, m), 5.30 (2H, brs), 6.10 (1H, t), 6.73–6.84 (3H, m), 7.01–7.03 (3H, m), 7.21–7.28 (2H, m), 7.59 (1H, dd), 8.48 (1H, dd). MS m/z: 483 (M+1).

Example 68

1-[3-(5,11-Dihydro-7-methoxypyrido[2,3-c][1]
benzoxepin-5-ylidene)propyl]-4-(2-keto-3-methyl-1-
imidazolinyl)piperidine The titled compound was prepared by following the procedure of example 36, but replacing of 4-(4-chlorophenyl)-1-[3-(6,11-dihydro-2-methoxydibenz[b,e]oxepin-11-ylidene)propyl]piperidin-4-ol with 1-[3-(5,11-dihydro-7-methoxypyrido[2,3-c][1]benzoxepin-5-ylidene)propyl]-4-(2-keto-1-imidazolinyl)piperidine.

$^1$H-NMR (CDCl$_3$) δ: 1.72–1.76 (2H, m), 2.09–2.14 (2H, m), 2.23–2.54 (6H, m), 2.91–2.96 (2H, m), 3.38 (3H, s), 3.77 (3H, s), 4.30–4.37 (1H, m), 5.27 (2H, brs), 6.08 (1H, t), 6.71–6.83 (3H, m), 6.93–7.06 (3H, m), 7.23–7.60 (2H, m), 8.08 (1H, dd), 8.48 (1H, dd). MS m/z: 497 (M+1).

Example 69

8-[3-(5,11-Dihydro-7-methoxypyrido[2,3-c][1]
benzoxepin-5-ylidene)propyl]-1-phenyl-1,3,8-
triazaspiro[4,5]decan-4-one The titled compound was prepared by following the procedure of example 45, step 3, but replacing 4-(4-chlorophenyl)-4-hydroxypiperidine with 1-phenyl-1,3,8-triazaspiro[4,5]decan-4-one.

$^1$H-NMR (CDCl$_3$) δ: 1.65–1.70 (2H, m), 2.36–2.41 (2H, m), 2.53–2.79 (8H, m), 3.76 (3H, s), 4.70 (2H, s), 5.25 (2H, brs), 6.10 (1H, t), 6.71–6.88 (6H, m), 7.21–7.27 (3H, m), 7.58–7.61 (2H, m), 8.48 (1H, dd). MS m/z: 497 (M+1).

Example 70

4-Anilino-4-carbamyl-1-[3-(5,11-dihydro-7-
methoxypyrido[2,3-c][1]benzoxepin-5-ylidene)
propyl]piperidine The titled compound was prepared by following the procedure of example 45, step 3, but replacing 4-(4-chlorophenyl)-4-hydroxypiperidine with 4-anilino-4-carbamylpiperidine.

$^1$H-NMR (CDCl$_3$) δ: 1.85–1.90 (2H, m), 2.03–2.08 (2H, m), 2.19–2.46 (6H, m), 2.62–2.67 (2H, m), 3.75 (3H, s), 3.97 (1H, brs), 5.27 (2H, brs), 5.53 (1H, brs), 6.03 (1H, t), 6.60 (2H, d), 6.70–6.85 (4H, m), 7.12–7.25 (4H, m), 7.53 (1H, dd), 8.46 (1H, dd). MS m/z 485 (M+1).

Example 71

1-(4-Chlorophenyl)-4-[3-(5,11-dihydro-7-
methoxypyrido[2,3-c][1]benzoxepin-5-ylidene)
propyl]piperazine The titled compound was prepared by following the procedure of example 45, step 3, but replacing 4-(4-chlorophenyl)-4-hydroxypiperidine with 1-(4-chlorophenyl)piperazine.

$^1$H-NMR (CDCl$_3$) δ: 2.36–2.53 (8H, m), 3.07–3.09 (4H, m), 3.76 (3H, s), 5.26 (2H, brs), 6.08 (1H, t), 6.72–6.81 (5H, m), 7.16–7.28 (3H, m), 7.56 (1H, dd), 8.49 (1H, dd). MS m/z: 462 (M+1).

Example 72

1-[3-(5,11-Dihydro-7-methoxypyrido[2,3-c][1]
benzoxepin-5-ylidene)propyl]-4-(2-pyrimidyl)
piperazine The titled compound was prepared by following the procedure of example 45, step 3, but replacing 4-(4-chlorophenyl)-4-hydroxypiperidine with 1-(2-pyrimidyl)piperazine.

$^1$H-NMR (CDCl$_3$) δ: 2.37–2.53 (8H, m), 3.74–3.83 (7H, m), 5.27 (2H, brs), 6.08 (1H, t), 6.45 (1H, t), 6.72–6.83 (3H, m), 7.25 (1H, dd), 7.56 (1H, dd), 8.27 (2H, d), 8.49 (1H, dd). MS m/z: 430 (M+1).

Example 73

1-Cyclohexyl-4-[3-(5,11-dihydro-7-methoxypyrido
[2,3-c][1]benzoxepin-5-ylidene)propyl]piperazine The titled compound was prepared by following the procedure of example 45, step 3, but replacing 4-(4-chlorophenyl)-4-hydroxypiperidine with 1-cyclohexylpiperazine.

$^1$H-NMR (CDCl$_3$) δ: 1.12–1.27 (6H, m), 1.74–1.86 (6H, m), 2.18–2.52 (11H, m), 3.76 (3H, s), 5.26 (2H, brs), 6.04 (1H, t), 6.74–6.81 (3H, m), 7.23 (1H, dd), 7.55 (1H, dd), 8.48 (1H, dd). MS m/z: 434 (M+1).

Example 74

1-[3-(5,11-Dihydro-7-methoxypyrido[2,3-c][1]
benzoxepin-5-ylidene)propyl]-4-(2-furoyl)piperazine The titled compound was prepared by following the procedure of example 45, step 3, but replacing 4-(4-chlorophenyl)-4-hydroxypiperidine with 1-(2-furoyl)piperazine.

$^1$H-NMR (CDCl$_3$) δ: 2.34–2.48 (8H, m), 3.71–3.74 (7H, s), 5.24 (2H, brs), 6.05 (1H, t), 6.42 (1H, dd), 6.70–6.80 (3H, m), 6.93 (1H, d), 7.23 (1H, dd), 7.42 (1H, d), 7.53 (1H, dd), 8.46 (1H, dd). MS m/z: 446 (M+1).

Examples 4–7, 9–11, 13–16, 20 and 75–139 shown in FIG. 6 can be prepared by the schemes set forth in FIGS. 1–5 and by the procedures described above.

Equivalents

Those skilled in the art will be able to recognize, or be able to ascertain, using no more than routine experimentation, many equivalents to the specific embodi-

What is claimed:

1. A compound represented by the following structural formula:

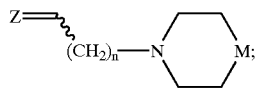

or physiologically acceptable salt thereof, wherein:

n is an integer from one to four;

M is >$CR^1R^2$;

$R^1$ is —H, —OH, an aliphatic group, —O-(aliphatic group), —O-(substituted aliphatic group), —SH, —S-(aliphatic group), —S-(substituted aliphatic group), —OC(O)-(aliphatic group), —O—C(O)-(substituted aliphatic group), —COOH, —CO—$NR^3R^4$ or —$NR^3R^4$; and $R^2$ is —OH, an acyl group, a substituted acyl group, —$NR^5R^6$, an aliphatic group, a substituted aliphatic group, an aromatic group, a substituted aromatic group, a benzyl group, a substituted benzyl group, a non-aromatic heterocyclic group or a substituted non-aromatic heterocyclic group; wherein:

$R^3$, $R^4$, $R^5$ and $R^6$ are independently an acyl group, a substituted acyl group, an aliphatic group, a substituted aliphatic group, an aromatic group, a substituted aromatic group, a benzyl group, a substituted benzyl group, a non-aromatic heterocyclic group or a substituted non-aromatic heterocyclic group; or $R^1$ and $R^2$, $R^3$ and $R^4$, or $R^5$ and $R^6$ taken together with the atom to which they are bonded, form a substituted or unsubstituted non-aromatic carbocyclic or heterocyclic ring;

said acyl group is selected from the group consisting of aliphatic carbonyl, aromatic carbonyl, aliphatic sulfonyl and aromatic sulfonyl;

Z is represented by the following structural formula:

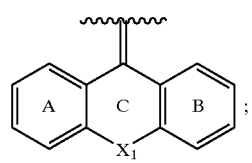

wherein:

$X_1$ is —$NR_c$—$CH_2$—, —$CH_2$—$NR_c$—, —$NR_c$—CO— or —CO—$NR_c$—;

$R_c$ is a substituted $C_1$–$C_{20}$ aliphatic group, an aromatic group, a substituted aromatic group, a benzyl group or a substituted benzyl group; and Ring A and Ring B are independently substituted or unsubstituted.

2. The compound of claim 1 wherein Ring A or Ring B has at least two substituents.

3. The compound of claim 1 wherein Ring A or Ring B is substituted with —OH, a halogen, a substituted aliphatic group, —O-(aliphatic group), —O-(substituted aliphatic group), —O-(aromatic group), —O-(substituted aromatic group), an electron withdrawing group, —(O)$_u$—(CH$_2$)$_t$—COOR$^{20}$, —(O)$_u$—(CH$_2$)$_t$—C(O)—NR$^{21}$R$^{22}$ or —(O)$_u$—(CH$_2$)$_t$—NHC(O)O—R$^{20}$; wherein:

said electron withdrawing group is alkylimine, alkylsulfonyl, carboxamido, carboxylic alkyl ester, —CH=NH, —CN or —NO$_2$;

$R^{20}$, $R^{21}$ or $R^{22}$ are independently —H, an aliphatic group, a substituted aliphatic group, an aromatic group, a substituted aromatic group or a non-aromatic heterocyclic group; or $R^{21}$ and $R^{22}$, taken together with the nitrogen atom to which they are bonded, form a non-aromatic heterocyclic ring;

u is zero or one; and t is an integer from zero to three.

4. The compound of claim 1 wherein $X_1$ is —$NR_c$—$CH_2$—, —$CH_2$—$NR_c$, —$NR_c$—CO—, or —CO—$NR_c$—;

$R_c$ is —(CH$_2$)$_s$—COOR$^{30}$, —(CH$_2$)$_s$—C(O)—NR$^{31}$R$^{32}$ or —(CH$_2$)$_s$—NHC(O)—O—R$^{30}$;

$R^{30}$, $R^{31}$ or $R^{32}$ are independently —H, an aliphatic group, a substituted aliphatic group, an aromatic group, a substituted aromatic group or a non-aromatic heterocyclic group; or $R^{31}$ and $R^{32}$, taken together with the nitrogen atom to which they are bonded, form a non-aromatic heterocyclic ring; and s is an integer from one to three.

5. The compound of claim 1 wherein:

n is two;

M is >C(OH)$R^2$; and $R^2$ is a substituted or unsubstituted aromatic group.

6. The compound of claim 5 wherein $R^2$ is an aromatic group substituted with halogen.

7. The compound of claim 6 wherein $R^2$ is a 4-chlorophenyl group.

8. A compound represented by the following structural formula:

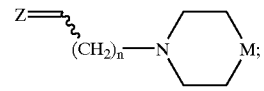

or physiologically acceptable salt thereof, wherein:

n is two;

M is >$CR^1R^2$;

$R^1$ is —OH;

$R^2$ is a 4-chlorophenyl group;

Z is represented by the following structural formula:

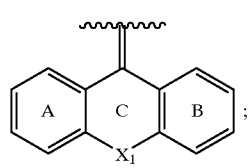

wherein:

$X_1$ is —$CH_2$—O—; and

Ring B is substituted with —C(CH$_3$)(OH)CH$_3$.

9. A compound represented by the following structural formula:

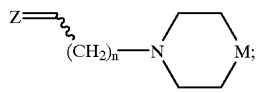

or physiologically acceptable salt thereof, wherein:
n is an integer from one to four;
M is $>CR^1R^2$;
$R^1$ is —H, —OH, an aliphatic group, —O-(aliphatic group), —O-(substituted aliphatic group), —SH, —S-(substituted aliphatic group), —OC(O)-(aliphatic group) or —O—C(O)-(substituted aliphatic group);
$R^2$ is an aliphatic group, a substituted aliphatic group, an aromatic group, a substituted aromatic group, a benzyl group, a substituted benzyl group, a non-aromatic heterocyclic group or a substituted non-aromatic heterocyclic group;
Z is represented by the following structural formula:

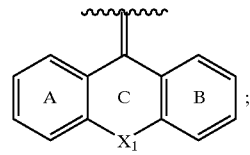

wherein:
$X_1$ is —$CH_2$—$NR_c$— or —CO—$NR_c$—;
$R_c$ is a substituted $C_1$–$C_{20}$ aliphatic group, an aromatic group, a substituted aromatic group, a benzyl group or a substituted benzyl group; and
Ring A and Ring B are independently substituted or unsubstituted.

* * * * *